US007198781B1

(12) United States Patent
Revel et al.

(10) Patent No.: US 7,198,781 B1
(45) Date of Patent: Apr. 3, 2007

(54) CHIMERIC INTERLEUKIN-6 SOLUBLE RECEPTOR/LIGAND PROTEINS

(75) Inventors: Michel Revel, Rehovot (IL); Judith Chebath, Rehovot (IL); Tsvee Lapidot, Ness-Ziona (IL); Orit Kollet, Ramat Gan (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 09/462,416

(22) PCT Filed: Jul. 9, 1998

(86) PCT No.: PCT/IL98/00321

§ 371 (c)(1),
(2), (4) Date: Apr. 13, 2000

(87) PCT Pub. No.: WO99/02552

PCT Pub. Date: Jan. 21, 1999

(30) Foreign Application Priority Data

Jul. 10, 1997 (IL) ..................................... 121284
Dec. 30, 1997 (IL) ..................................... 122818

(51) Int. Cl.
*A61K 38/20* (2006.01)
*A61K 38/16* (2006.01)
(52) U.S. Cl. .................... 424/85.2; 530/350; 530/351; 514/12
(58) Field of Classification Search ................ 530/300, 530/350; 435/69.51, 69.7, 69.1; 536/23.1
See application file for complete search history.

(56) References Cited

U.S. PATENT DOCUMENTS 6,372,207 B1 * 4/2002 Tepper et al. ............... 424/85.4

FOREIGN PATENT DOCUMENTS

| EP | 0 413 908 | 2/1991 |
| EP | 0 538 810 | 4/1993 |
| EP | 0 888 384 B1 | 12/2002 |
| WO | 96 36354 | 11/1996 |
| WO | 97 32891 | 9/1997 |

OTHER PUBLICATIONS

Lust, J.A. et al. 1995, Sequence, expression and function of an mRNA encoding a soluble form of the human interleukin-6 receptor (sIL-6R). Curr Top Microbiol Immunol. 194:199-206.*
Sambrook, J. et al. 1989. Molecular cloning—a laboratory manual. Cold Spring Harbor Press. pp. 9.47-9.51 and 11.38-11.49.*
Yawata, H et al. 1993. Structure-function analysis of human IL-6 receptor: dissociation of amino acid resudues required for IL-6-binding and for IL-6 signal transduction through gp130. EMBO J 12(4):1705-1712.*
Paonessa, G. et al. 1995. Two distinct and independent sites on IL-6 trigger gp130 dimer formation and signalling. EMBO J 14(9):1942-1951.*
Mazumder, B. et al. 2003. Translational control by the 3' UTR: the ends specify the means. Trends in Biochemical Sciences 28:91-98.*
Weich et al. 1993. Experimental Hematology 21:647-655.*
Chen et al. 1997. Proc Natl Acad Sci USA 94:6910-6915.*
Chebath et al., "Interleukin-6 receptor-interleukin-6 fusion proteins with enhanced interleulin-6 type pleiotropic activities", *Eur. Cytokine News*, vol. 8, No. 4, pp. 359-365, (1997).
Sui et al., "gp130 and c-Kit signaling synergize for ex vivo expansion of human primitives hemopoietic progenitor cells", *Proc. Natl., Acad. Sci.*, vol. 92, pp. 2859-2863, (1995).
Mackiewicz et al., "Interleukin-6-Type Cytokines and Their Receptors for Gene Therapy of Melanoma", pp. 361-374, (1995).
Fischer et al., A bioactive designer cytokine for human hematopoietic progenitor cell expansion, *Nature Biotechnology*, vol. 15, pp. 142-144, (1997).
Kollet et al., "Soluble IL-6 receptor/IL-6 fusion protein enhance maintenance and proliferation of human CD34/CD38 stem cells in vitro", pp. 394, (1997).
Kollet, O., et al. Blood. 90 (10 Suppl. 1 part 1), Nov. 15, 1997; 394A.
Mackiewicz, A., et al. Ann. NY Acad. Sci. Jul. 21, 1995; 762:361-73; discussion 373-4.

* cited by examiner

*Primary Examiner*—Janet Andres
*Assistant Examiner*—Daniel E. Kolker
(74) *Attorney, Agent, or Firm*—Browdy and Neimark, PLLC

(57) ABSTRACT

Chimeric proteins constructed from the fusion of the naturally occurring form of the soluble IL-6 receptor and IL-6 which are useful for treatment of cancer and liver disorders, enhancement of bone marrow transplantation, and treatment of other IL-6 related conditions are provided.

7 Claims, 15 Drawing Sheets

```
         . 10       . 20      . 30      . 40      . 50      . 60
MLAVGCALLAALLAAPGAALAPRRCPAQEVARGVLTSLPGDSVTLTCPGVEPEDNATVHW
    signal peptide                            Ig-like domain
         . 70       . 80      . 90     . 100     . 110     . 120
VLRKPAAGSHPSRWAGMGRRLLLRSVQLHDSGNYSCYRAGRPAGTVHLLVDVPPEEPQLS . 130      . 140     . 150     . 160     . 170     . 180
CFRKSPLSNVVCEWGPRSTPSLTTKAVLLVRKFQNSPAEDFQEPCQYSQESQKFSCQLAV
                       cytokine receptor N-domain
        . 190      . 200     . 210     . 220     . 230     . 240
PEGDSSFYIVSMCVASSVGSKFSKTQTFQGCGILQPDPPANITVTAVARNPRWLSVTWQD . 250      . 260     . 270     . 280     . 290     . 300
PHSWNSSFYRLRFELRYRAERSKTFTTWMVKDLQHHCVIHDAWSGLRHVVQLRAQEEFGQ
                       cytokine receptor C-domain
        . 310      . 320     . 330     . 340     . 350     . 360
GEWSEWSPEAMGTPWTESRSPPAENEVSTPMQALTTNKDDDNILFRDSANATSLPVEFMP
                       receptor pre-membrane region
        . 370      . 380     . 390     . 400     . 410     . 420
VPPGEDSKDVAAPHRQPLTSSERIDKQIRYILDGISALRKETCNKSNMCESSKEALAENN
                              IL-6
        . 430      . 440     . 450     . 460     . 470     . 480
LNLPKMAEKDGCFQSGFNEETCLVKIITGLLEFEVYLEYLQNRFESSEEQARAVQMSTKV . 490      . 500     . 510     . 520     . 530     . 540
LIQFLQKKAKNLDAITTPDPTTNASLLTKLQAQNQWLQDMTTTHLILRSFKEFLQSSLRALRQM
```

Fig. 3

```
      *          *          *          *          *          *
  1 MNSFSTSAFGPVAFSLGLLLVLPAAFPAPVPPGEDSKDVAAPHRQPLTSSERIDKQIRYI  60
 61 LDGISALRKETCNKSNMCESSKEALAENNLNLPKMAEKDGCFQSGFNEETCLVKIITGLL 120
121 EFEVYLEYLQNRFESSEEQARAVQMSTKVLIQFLQKKAKNLDAITTPDPTTNASLLTKLQ 180
181 AQNQWLQDMTTHLILRSFKEFLQSSLRALRQMGGGGDPGGGGGGPGVPPEEPQLSCFRKS 240
241 PLSNVVCEWGPRSTPSLTTKAVLLVRKFQNSPAEDFQEPCQYSQESQKFSCQLAVPEGDS 300
301 SFYIVSMCVASSVGSKFSKTQTFQGCGILQPDPPANITVTAVARNPRWLSVTWQDPHSWN 360
361 SSFYRLRFELRYRAERSKTFTTWMVKDLQHHCVIHDAWSGLRHVVQLRAQEEFGQGEWSE 420
421 WSPEAMGTPWTESRSPPAENEVSTPMQALTTNKDDDNILFRDSANATSLPV*         471
```

Fig. 11

CHIMERIC INTERLEUKIN-6 SOLUBLE RECEPTOR/LIGAND PROTEINS

CROSS REFERENCE TO RELATED APPLICATION

The present application is the national stage under 35 U.S.C. 371 PCT/IL98/00321, filed 9 Jul. 1998.

FIELD OF THE INVENTION

The present invention is generally in the field of interleukin-6 (IL-6) biological activities which are dependent on the agonistic action of soluble IL-6 receptor (sIL-6R). More specifically, the present invention concerns novel chimeric sIL-6R/IL-6 proteins constructed from the fusion of essentially the naturally occurring form of sIL-6R and IL-6, and biologically active analogs thereof, which are particularly useful for treating cancer, via inhibition of cancerous cell growth, for enhancing bone marrow transplantation, for treating liver disorders and other IL-6 related conditions.

BACKGROUND OF THE INVENTION AND PRIOR ART

Interleukin-6 (IL-6) is a well known cytokine whose biological activitities are mediated by a membranal receptor system comprising two different proteins one named IL-6 Receptor (IL-6R or gp80) and the other gp130(reviewed by Hirano et al, 1994). Soluble forms of IL-6R (sIL-6R), corresponding to the extracellular domain of gp80, are natural products of the human body found as glycoproteins in blood and in urine (Novick et al, 1990, 1992). An exceptional property of sIL-6R molecules is that they act as potent agonists of IL-6 on many cell types including human cells (Taga et al, 1989; Novick et al, 1992). This is due to the fact that even without the intracytoplasmic domain of gp80, sIL-6R is still capable of triggering the dimerization of gp130 in response to IL-6, which in turn mediates the subsequent IL-6-specific signal transduction and biological effects (Murakami et al, 1993). The active IL-6 receptor complex is in fact a hexameric structure formed by two gp130 chains, two IL-6R and two IL-6 ligands (Ward et al, 1994; Paonessa et al, 1995), in which sIL-6R has two types of interaction with gp130 both of which are essential for the IL-6-specific biological activities (Halimi et al, 1995).

Treatment with sIL-6R results in an enhancement of the biological activities of IL-6 in many cell types. An example is tumor cells whose growth is inhibited to a greater extent by IL-6 when sIL-6R is added, such as murine myeloleukemic M1 cells (Taga et al, 1989), human breast carcinoma T47D cells (Novick et al, 1992) or human Non-small cell lung carcinoma cells (Ganaphthi et al, 1996). IL-6 has anti-metastatic activities in vivo (Katz et al, 1995), sIL-6R and can also enhance such in vivo anti-tumor effects of IL-6 (Mackiewicz et al 1995). Another activity of IL-6 which is enhanced by sIL-6R addition, is the stimulation of hematopoietic stem cells to produce multilineage colonies (Sui et al, 1995). The present inventors have also observed that the survival of primary cultures of brain oligodendrocytes is supported by the sIL-6R and IL-6 combination (Oh, 1997), while IL-6 alone is poorly active in such cultures (Kahn and De Vellis, 1994). This finding indicates that IL-6, when combined with sIL-6R, can mimic the activity of other neurotropic cytokines such as Ciliary Neurotropic Factor (CNTF) or Leukemia Inhibitory Factor (LIF) which also act through gp130, as is also the case for IL-11 and Oncostatin M (Hirano et al, 1994).

In an attempt to provide a molecule which may combine the above noted functions of IL-6 and sIL-6R, there has recently been reported the production in recombinant yeast cells of a fusion protein between a truncated segment of the human IL-6R sequence and IL-6, linked by a glycine-rich linker (Fischer et al., 1997). This fusion protein includes essentially only the IL-6R cytokine receptor N-domain and the cytokine receptor C-domain, and thus lacks essentially all of the IL-6R immunoglobulin (Ig)-like domain, and the receptor pre-membrane region (the region between the C-domain and the transmembranal domain). As such it represents a truncated form of the sIL-6R, this truncated sIL-6R in the fusion protein being linked via the above noted glycine-rich linker to essentially the whole mature form of IL-6. Besides lacking parts of the natural sIL-6R, this fusion protein by being produced in yeast cells, does not have the glycosylation pattern that such a fusion protein would have if it were produced in mammalian cells, in particular, e.g. in human cells. In fact, this yeast-produced fusion protein has a molecular weight of only about 57 kDa in contrast to a fusion product containing essentially all of the natural sIL-6R and IL-6 amino acid residues and being fully glycosylated in mammalian (e.g. human) cells, which has the expected molecular weight of about 85 kDa (see Example 2 herein below).

The common experience in developing recombinant proteins which can be used for treating human patients has shown that it is important to remain as close as possible to the natural forms of the proteins, as they are found in the human body, in order to avoid triggering of antibodies and other side effects observed with non-natural recombinant products. For this reason, it has been advantageous to use recombinant mammalian cell systems to produce glycosylated proteins such as Interferon-β or Granulocyte-colony stimulating factor (Chernajovsky et al, 1984, Holloway, 1994) in a chemical form as similar as possible to the natural human product. Bacteria or microorganisms such as, for example, yeasts, which do not glycosylate properly, also cause the wrong folding of the protein chains, leading to immunogenic reactions. This is particularly important in respect of IL-6 which is heavily modified postranslationally by N- and O-glycosylation as well as by phosphorylation (Revel, 1989 for review), and in respect of the natural sIL-6R from human blood and urine which is a glycoprotein whose N-terminus and C-terminal amino-acids are constant and have been determined (Novick et al, 1990 and co-owned patents by the present inventors Nos. U.S. Pat. No. 5,216, 128 and its corresponding EP 413908 B1).

Accordingly, it would seem that the above noted previous fusion product between part of the sIL-6R and IL-6 has a number of possible drawbacks especially as regards its use for treating humans and this, due to the fact that it lacks part of the sIL-6R, as well as its production in yeasts which may provide for incorrect glycosylation of the protein.

Heretofore, a fusion molecule comprising the natural sIL-6R found in human body fluids and the natural IL-6, and which is produced in human or other mammalian cells, has not been described.

It is therefore an aim of the present invention to provide such a fusion molecule comprising the natural sIL-6R and the natural IL-6 (in any order) which is produced in mammalian cells.

It is another aim of the present invention to use such a fusion protein (sIL-6R/IL-6 chimera) to inhibit the growth of highly metastatic melanoma cells at very low concentrations, these cells being resistant to IL-6 or sIL-6R alone.

Yet another aim is to use such a fusion protein (the sIL-6R/IL-6 chimera) for the in vivo engraftment of human hematopoietic stem cells in bone marrow transplantation protocols.

It is a yet further aim of the present invention to use such a fusion protein in other IL-6 related disorders, e.g. liver conditions or neurological conditions.

A further aim of the invention is to provide pharmaceutical compositions which contain the above mentioned natural sIL-6R-natural IL-6 fusion protein (sIL-6R/IL-6 chimera) for the treatment of cancer, for use in bone marrow transplantation procedures, and for other IL-6 related disorders, e.g. liver conditions and neurological conditions.

Other aims and aspects of the present invention will be set forth or will arise from the following disclosure of the present invention.

SUMMARY OF THE INVENTION

In accordance with the present invention there have been produced a number of fusion proteins (chimeras) each comprising essentially all of the naturally occurring sIL-6R from human body fluids and essentially all of the mature form of the naturally occurring human IL-6, and each joined by short linker peptides which can be as short as 3 amino acid residues in length or longer, for example, 13 amino acid residues in length (see below and Examples 1 and 2). It should be noted, however, that in these fusion proteins the linker peptides may be ommitted and the sIL-6R moiety may be directly linked to the IL-6 moiety. Since linkers representing non-natural amino acid sequences may be immunogenic epitopes eliciting antibodies in patients, it is preferable to have a directly fused sIL-6R/IL-6 chimera that has the desired biological activity, while at the same time there is minimized the risk of inducing such potentially deleterious antibody formation when such a chimera is administered.

The conservation of the entire sIL-6R sequence including the Ig-like domain as found in the naturally occurring molecule, as well as the proper glycosylation and other post-translational modifications introduced by human or mammalian cells when the above chimera is produced in such cells, are also important to reduce the potential immunogenicity of the chimeric protein product.

However, it is possible to use a very short linker of about three amino acids at the junction point between the sIL-6R and IL-6 moieties of the chimeric protein. Such a short linker would not be an immunogenic epitope. It is of course also possible to use longer linkers of up to about 30 amino acids to provide for separation between the two moieites but here care must be taken and biological efficacy and safety experiments must be performed to ensure that chimeric molecules with such linkers are not immunogenic.

In fact, it has been surprisingly shown in accordance with the present invention that such longer linkers are not essential for the activity of the chimeric protein indicating that proper folding of the chimera does not require a longer linker especially when essentially all of the naturally-occurring sequences of the sIL-6R and IL-6 moieties are incorporated into the chimeric molecule (see Example 3 and FIG. 5 which relate also to a comparison between a sIL-6R/IL-6 chimera having a very short (3 amino acids) linker and a similar chimera having a longer linker of 30 amino acids).

These fusion proteins or sIL-6R/IL-6 chimeras have been efficiently produced, in accordance with the present invention, in mammalian cell expression systems to yield glycosylated products having potent activity on tumor cells which are usually non-responsive to IL-6 or sIL-6R alone, and which were highly effective in ensuring the success of engraftment of human bone marrow transplanted cells (see below and Examples 1–4). In fact, in such bone marrow transplants, the sIL-6R/IL-6 chimeras were essential for the survival and proliferation of the transplanted non-committed pluripotential hematopoietic stem cells. Moreover, from the experimental results presented herein below, as well as from other analyses it arises that various analogs of the sIL-6R/IL-6 chimeric protein of the invention can be prepared, which have essentially the same biological activity of the sIL-6R/IL-6 chimera, these analogs being sIL-6R/IL-6 chimeras in which one or more amino acid residues have been deleted, added or substituted by others, the only limitation on such analogs being that they retain most of the naturally occurring sIL-6R and IL-6 sequence. For example, amino acid additions to the naturally occurring sIL-6R and IL-6 sequences are preferably limited to up to between about 20 amino acids, and preferably these additions are at the site of junction between the sIL-6R and IL-6, i.e. the linker molecule. Likewise, deletions from the sIL-6R and IL-6 sequences are preferably limited to up to between about 20–30 amino acids; and substitutions of amino acid residues in the sIL-6R and IL-6 sequences by other amino acid residues are preferably also limited to up to between about 20–30 amino acids. All of the aforesaid deletions, additions and substitutions are acceptable in accordance with the present invention when the so-modified analogs that are obtained retain essentially the biological activity of the sIL-6R/IL-6 chimera composed of essentially the naturally-occurring sequences, and retain essentially the same glycosylation pattern of the chimera composed of essentially the naturally-occurring sequences when expressed in mammalian cells.

Accordingly, the present invention provides a chimeric glycosylated soluble interleukin-6 receptor (sIL-6R)-interleukin-6 (IL-6) protein (sIL-6R/IL-6) and biologically active analogs thereof, comprising a fusion protein product between essentially all of the naturally occurring form of sIL-6R and essentially all of the naturally occurring form of IL-6, said sIL-6R/IL-6 and analogs thereof being glycosylated in a similar fashion to the glycosylation of naturally occurring sIL-6R and IL-6.

Embodiments of the above chimeric protein of the invention include (i) A chimeric sIL-6R/IL-6 protein and biologically active analogs thereof, wherein said sIL-6R is fused to IL-6 via a peptide linker molecule.

(ii) A chimeric sIL-6R/IL-6 protein and biologically active analogs thereof, as in (i) above, wherein said linker is a very short, non-immunogenic linker of about 3–4 amino acid residues.

(iii) A chimeric sIL-6R/IL-6 protein and biologically active analogs thereof, as in (ii) above, wherein said linker is a tripeptide of the sequence E-F-M (Glu-Phe-Met).

(iv) A chimeric sIL-6R/IL-6 protein and biologically active analogs thereof, as in (i) above, wherein said linker is a peptide of 13 amino acid residues of sequence E-F-G-A-G-L-V-L-G-G-Q-F-M (Glu-Phe-Gly-Ala-Gly-Leu-Val-Leu-Gly-Gly-Gln-Phe-Met) (SEQ ID:NO 1).

(v) A chimeric sIL-6R/IL-6 protein, being the herein designated sIL-6RδVal/IL-6 having a tripeptide linker of sequence E-F-M between the C-terminal Val-356 of sIL-6R and the N-terminal Pro-29 of IL-6, said chimeric protein having the sequence set forth in FIG. 3.

(vi) A chimeric sIL-6R/IL-6 protein, being the herein designated sIL-6RδVal/L/IL-6 having a 13 amino acid peptide linker of sequence E-F-G-A-G-L-V-L-G-G-Q-F-M (SEQ ID NO:1) between the C-terminal Val-356 of sIL-6R and the N-terminal Pro-29 of IL-6, said chimeric protein having the sequence of SEQ ID NO:13, i.e., the sequence set forth in FIG. 3 wherein the tripeptide of sequence E-F-M at positions 357–359 of FIG. 3 is replaced by said 13 amino acid peptide sequence.

(vii) A chimeric sIL-6R/IL-6 protein, wherein said protein is produced in mammalian cells in a fully processed form.

(viii) A chimeric sIL-6R/IL-6 protein, wherein said protein is produced in human cells.

(ix) A chimeric sIL-6R/IL-6 protein, wherein said protein is produced in CHO cells.

(x) A chimeric sIL-6R/IL-6 protein and biologically active analogs thereof, as above, wherein said chimeric protein and analogs are characterized by being capable of inhibiting the growth of highly malignant cancer cells.

(xi) A chimeric sIL-6R/IL-6 protein and biologically active analogs thereof, as above, wherein said chimeric protein and analogs are characterized by being capable of inhibiting the growth of highly malignant melanoma cells.

(xii) A chimeric sIL-6R/IL-6 protein and biologically active analogs thereof, as above, wherein said chimeric protein and analogs are characterized by being capable of eliciting the in vivo engraftment of human hematopoietic cells in bone marrow transplantations.

(xiii) A chimeric sIL-6R/IL-6 protein and biologically active analogs thereof, as above, wherein said chimeric protein and analogs are characterized by being capable of protecting liver against hepatotoxic agents.

The present invention also provides a DNA sequence encoding a chimeric sIL-6R/IL-6 protein and biologically active analogs thereof as noted above according to the invention.

In addition, the present invention also provides a DNA vector comprising a DNA sequence encoding a chimeric sIL-6R/IL-6 protein and biologically active analogs thereof of the invention, as noted above, said vector being suitable for expression of said chimeric protein in mammalian cells.

Embodiments of the DNA vector of the invention include:

(i) A DNA vector wherein said vector is suitable for expression of said chimeric protein in human cells.

(ii) A DNA vector wherein when said vector is expressed in mammalian or human cells, the expressed chimeric protein has a sequence that permits full processing of the chimeric protein by the mammalian or human cell and secretion of the fully processed chimeric protein from the cells into the culture medium in which said cells are grown.

(iii) A DNA vector, as above, wherein said vector is the herein designated plasmid pcDNAsIL-6R/IL-6 comprising a pcDNA3 vector containing the DNA sequence encoding the chimeric sIL-6R/IL-6 protein under the control of a cytomegalovirus (CMV) promoter.

(iv) A DNA vector, as above, wherein said vector is the herein designated plasmid pcDNA sIL-6R/L/IL-6 comprising a pcDNA3 vector containing the DNA sequence encoding the chimeric sIL-6R/IL-6 protein under the control of a cytomegalovirus (CMV) promoter, and wherein in said DNA sequence encoding said chimeric sIL-6R/IL-6 protein there is inserted a linker sequence encoding a linker peptide at the EcoRI site placed between the sequence encoding the sIL-6R part and the sequence encoding the IL-6 part of the protein.

Likewise, the present invention also provides transformed mammalian cells containing a DNA vector as above, that is capable of expressing the sIL-6R/IL-6 chimeric protein sequence carried by said vector and of fully processing the expressed protein and secreting it into the culture medium in which said cells are grown.

An embodiment of these transformed cells are the herein described human embryonal kidney cells 293 (HEK293) transfected by the pcDNA sIL-6R/II-6 vector, said cells being capable of expressing the sIL-6R/IL-6 chimeric protein, fully processing said protein and secreting said protein into the culture medium in which said cells are grown in the form of an about 85 kDa glycoprotein.

Another embodiment of transformed cells are the herein described CHO (Chinese Hamster Ovary) cells transfected by the pcDNA sIL-6R/IL-6 vector, said cells being capable of expressing the sIL-6-R/IL-6 chimeric protein, fully processing said protein into the culture medium in which said cells are grown in the form of an about 85 kDa glycoprotein.

The present invention also provides a method for producing a chimeric protein or biologically active analogs thereof, as above, comprising growing the aforesaid transformed cells under conditions suitable for expression, processing and secretion of said protein or analogs into the culture medium in which said cells are grown; and purifying said protein or analogs from said culture medium by immunoaffinity chromatography using monoclonal antibodies specific for sIL-6R.

The chimeric protein of the present invention has a number of uses including:

(i) use of a chimeric sIL-6R/IL-6 protein or analogs, salts of any one thereof, and mixtures thereof, as an inhibitor of cancer cells.

(ii) use, as in (i) above, as an inhibitor of highly malignant melanoma cells.

(iii) use of a chimeric sIL-6R/IL-6 protein or analogs, salts of any one thereof, and mixtures thereof, as an active ingredient for eliciting engraftment of human hematopoietic cells in bone marrow transplantation.

(iv) use of a chimeric sIL-6R/IL-6 protein or analogs, salts of any one thereof, and mixtures thereof, as an active ingredient for increasing hematopoiesis, for treating hepatic and neurological conditions, or for other applications in which IL-6 or sIL-6R are used.

Similarly, the chimeric protein of the present invention may be used to prepare medicaments for a number of medical indications, namely, a chimeric sIL-6R/IL-6 protein or analogs, salts of any one thereof and mixtures thereof, for use in the preparation of a medicament for treating cancers by way of inhibition of cancer cells, or in the preparation of a medicament for enhancement of bone marrow transplantation by way of eliciting engraftment of human hematopoietic cells in bone marrow transplantation, or in the preparation of a medicament for increasing hematopoeisis, or in the preparation of a medicament for treating neurological disorders, or in the preparation of a medicament for other applications in which IL-6 or sIL-6R are used.

Moreover, the present invention also provides a pharmaceutical composition comprising as active ingredient a chimeric sIL-6R/IL-6 protein or analog thereof as above, and a pharmaceutically acceptable carrier, diluent or excipient.

Embodiments of this pharmaceutical composition of the invention include:

(i) A pharmaceutical composition for the treatment of mammalian cancers.

(ii) A pharmaceutical composition for the enhancement of bone marrow transplantation.

(iii) A pharmaceutical composition for the treatment of liver and neurological disorders, or for increasing hematopoeisis or for other applications in which IL-6 or sIL-6R are used.

The present invention also provides for a method for treating cancers in mammals, or for enhancing bone marrow transplantations, or for treating hepatic and neurological disorders, or for increasing hematopoiesis, or for other applications in which IL-6 or sIL-6R are used, comprising administering to a patient a pharmaceutical composition, as above, in a suitable dosage form and by a suitable route of administration.

In order to avoid doubt, the present invention relates to a chimera between IL-6 and sIL-6R in any order, i.e. the N-terminal and C-terminal portions may be reversed and the chimera is then an IL-6-sIL-6R protein, although it is referred to herein as sIL-6R/IL-6 protein throughout.

Other aspects and embodiments of the present invention are set forth or arise directly from the following detailed disclosure of the invention.

BRIEF DESCRIPTION OF THE DRAWINGS

FIG. 3 depicts the amino acid sequence (one-letter code) (SEQ ID NO:7) of the sIL-6RδVal/IL-6 chimera in which is shown the different domains of the molecule, including the N-terminal signal peptide (line on top of sequence), the immunoglobulin-like (Ig-like) domain, the cytokine receptor N-domain (underlined), the cytokine C-domain (line on top of sequence) and the receptor pre-membrane region (the region between the C-domain and the transmembranal domain), all of the sIL-6R part of the chimera; as well as the mature IL-6 moiety (underlined below) of the chimera, as described in Examples 1 and 2;

FIG. 11 depicts the amino acid sequence (one letter code) (SEQ ID NO:8) of the IL-6-sIL-6RδVal chimera 3e, the linker being underlined.

DETAILED DESCRIPTION OF THE INVENTION

Figure 1A:
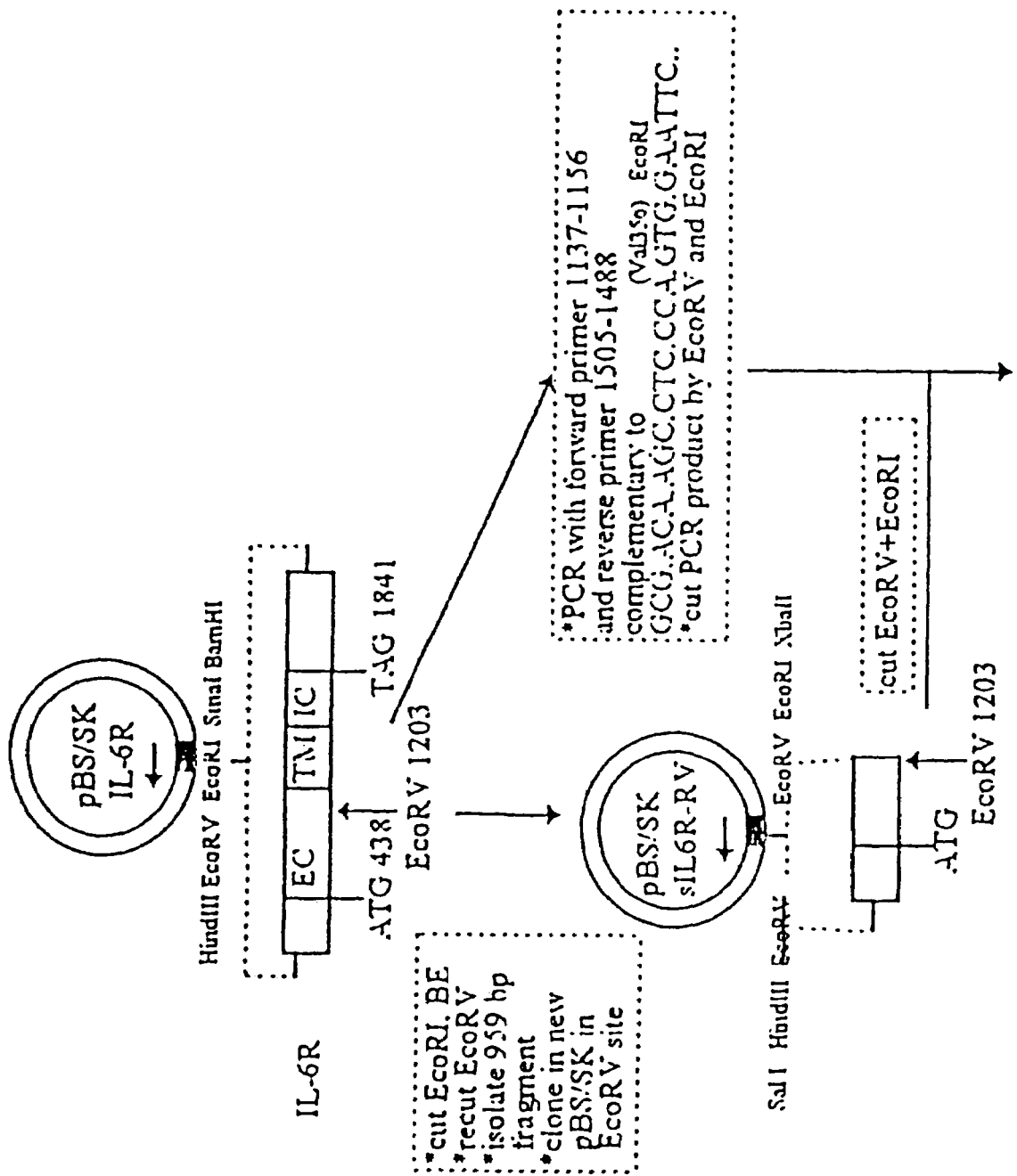
In FIG. 1A, the sequence after "*PCR with forward . . . complementary to" is SEQ ID NO:9 and in FIG. 1B, the sequence after "Processed IL-6 cDNA in E. coli expression vector" is SEQ ID NO:10.

The present invention concerns a chimeric sIL-6R/IL-6 protein and biologically active analogs thereof which have essentially all of the naturally occurring forms of sIL-6R and essentially all of the naturally occurring forms of IL-6 fused together, the site of fusion of which may be by way of a linker peptide, as short as 3 amino acids, and which chimeric sIL-6R/IL-6 protein or analogs have a similar amount and pattern of glycosylation as that of naturally occurring sIL-6R and IL-6. Such a chimeric sIL-6R/IL-6 protein produced in accordance with the present invention in mammalian cells, in particular, in human cells (see Examples 1–4 below) or CHO cells (see Example 6 below) was found to be efficiently expressed in such cells, to be highly glycosylated, and to have potent activity on tumor cells which show no response at all to IL-6 or sIL-6R alone.

More particularly, in accordance with the present invention it has been observed (see Examples 1–3 below) that the aforesaid chimeric sIL-6R/IL-6 protein of the invention causes growth arrest of highly malignant mammalian cells such as the F10.9 melanoma cells at concentrations lower than needed when a mixture of non-fused sIL-6R and IL-6 is used. This is a particularly significant result in view of the fact that such F10.9 melanoma cells continue to grow normally when treated with only IL-6 or only sIL-6R separately, and undergo growth arrest only when exposed to relatively high dosages of a combination of non-fused IL-6 and sIL-6R. Accordingly, the chimeric sIL-6R/IL-6 protein of the present invention is surprisingly a more potent inhibitor of these highly malignant melanoma cells than a mixture of its separate parts, i.e. a mixture of non-fused IL-6 and sIL-6R. The chimeric protein of the present invention is thus particularly useful as an active ingredient for treating various kinds of cancers.

The higher activity of the chimeric sIL-6R/IL-6 protein is accounted for by its higher affinity for gp130 than that of the mixture of non-fused IL-6 and sIL-6R (Example 7).

Furthermore, it has also been found in accordance with the present invention (see Example 4 below) that a chimeric sIL-6R/IL-6 molecule of the present invention is particularly useful for enhancing bone marrow transplantation. In fact, using a known protocol for engraftment of human bone marrow cells into severe combined immunodeficient (SCID) mice, in which stem-cell factor (SCF) and Flt3-ligand are used for enabling survival and proliferation of the most primitive pluripotential hematopoietic stem cells capable of long-term engraftment into recipient bone marrow, it was found that these two factors, SCF and Flt3-ligand, were insufficient to promote the engraftment of human cells into the receipient mouse bone marrow, and that only when the chimeric sIL-6R/IL-6 protein was also added was engraftment successful. This finding indicates that the chimeric protein may be essential in such engraftment protocols. In the same experiments, non-fused IL-6 and sIL-6R when added separately, were insufficient to promote successful bone marrow transplantation and when added together were much less active than the chimeric sIL-6R/IL-6 protein, i.e. at an effective concentration of 100 ng/ml the sIL-6R/IL-6 chimeric protein promoted successful bone marrow transplantation, while the two separate non-fused sIL-6R and IL-6 when added together at even higher concentrations (sIL-6R from 125–1250 ng/ml, IL-6 from 50–200 ng/ml), were much less active in promoting such transplantation.

The above chimeric sIL-6R/IL-6 protein of the invention is preferably a recombinant glycosylated sIL-6R/IL-6 chimera produced in human cells or in any other suitable mammalian cell expression system such as hamster CHO cells which is capable of glycosylating proteins as do human cells and which introduces the same post-translational modifications as do human cells. An important characteristic is that the chimeric glycoprotein so-produced is processed and modified as are the natural sIL-6R and IL-6 parent molecules found in the human body, without truncation and without addition of extraneous unnatural polypeptide sequences, with the exception of the very short tripeptide or when a longer linker peptide is incorporated between the sIL-6R and IL-6 moieties of the chimeric protein.

To prepare the above preferred chimeric protein of the invention, the following features of the naturally-occurring sIL-6R and IL-6 were considered: It is known that the IL-6R present in human cell membranes is produced by a cDNA encoding 468 aminoacids comprising a signal peptide, an Immunoglobulin (Ig) like domain, a cytokine binding domain, a transmembrane region and a cytoplasmic domain (Yamasaki et al, 1988). A soluble form of sIL-6R is found in body fluids which has, like the mature IL-6R from membranes, an N-terminus corresponding to Leu-20 (Novick et al, 1990) and a C-terminus corresponding to Val-356 just before the transmembrane region of IL-6R (see co-owned U.S. Pat. No. 5,216,128 and EP 413.908 B1). In order to fuse this sIL-6R sequence to IL-6, an EcoRI restriction site was introduced following Val-356. The sequence of the mature IL-6 starting at Pro-29 of the IL-6 cDNA and ending at Met-212 (Zilberstein et al, 1986; Hirano et al, 1986) was introduced after this EcoRI site. At this EcoRI site there could also, but not necessarily, be introduced a linker peptide of desired length to distance the sIL-6R and IL-6 moieties from each other in the chimeric protein. As set forth in the Examples below, two different chimeric proteins were produced as examples of such possible chimeric proteins, one having a tripeptide linker and the other having a 13-amino acid residue linker at this EcoRI site, both being essentially equally active biologically.

The present invention also concerns analogs of the above chimeric sIL-6R/IL-6 protein of the invention, which analogs retain essentially the same biological activity of the chimeric protein having essentially only the naturally-occurring sequences of sIL-6R and IL-6. Such analogs may be ones in which up to about 30 amino acid residues may be deleted, added or substituted by others in the sIL-6R and/or IL-6 moieties of the chimeric protein, such that modifications of this kind do not substantially change the biological activity of the chimeric protein analog with respect to the chimeric protein itself and in which the sIL-6R moiety of such analogs essentially retains the naturally occurring structure (before processing—see FIG. 3) of a signal peptide, Ig-like domain, cytokine receptor N-domain, cytokine receptor C-domain, and receptor pre-membrane domain. Likewise, such chimeric protein analogs should retain essentially the naturally-occurring mature form of the IL-6 moiety. The various analogs may differ most from each other and from the basic chimeric protein molecule (that with essentially only naturally-occurring sIL-6R and IL-6 sequences) at the site of the linker peptide which joins the sIL-6R and IL-6 moieties in the chimeric protein. Such a linker may be up to about 30 amino acids in length, and serves to separate the sIL-6R and IL-6 moieties from each other in the chimeric protein. As regards such a linker, care should be taken to choose its sequence (and hence also to test biologically in appropriate standard assays each such analog) such that it will, for example, not result in incorrect folding of the chimeric protein which may render it inactive, or it will not result in rendering the chimeric protein analog an immunogenic protein which will elicit antibodies against it in a patient to be treated therewith with the result that such an analog will be ineffective at least as a medium- or long-term medicament.

As regards the above analogs of the chimeric protein of the invention, these analogs are those in which one or more and up to about 30 of the amino acid residues of the basic chimeric protein of the invention are replaced by different amino acid residues, or are deleted, or one or more amino acid residues are added to the original sequence of chimeric protein of the invention (that with essentially only the naturally-occurring sIL-6R and IL-6 sequences) without changing considerably the activity of the resulting products as compared with the basic chimeric protein of the invention. These analogs are prepared by known synthesis and/or by site-directed mutagenesis techniques, or any other known technique suitable therefor.

Any such analog preferably has a sequence of amino acids sufficiently duplicative of that of the basic sIL-6R/IL-6 chimera such as to have substantially similar activity thereto. Thus, it can be determined whether any given analog has substantially the same activity as the basic chimeric protein of the invention by means of routine experimentation comprising subjecting such an analog to the biological activity tests set forth in Examples 2–4 below.

Analogs of the chimeric protein which can be used in accordance with the present invention, or nucleic acids coding therefor, include a finite set of substantially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., *Principles of Protein Structure*, Springer-Verlag, New York, 1978; and Creighton, T. E., *Proteins: Structure and Molecular Properties*, W.H. Freeman & Co., San Francisco, 1983, which are hereby incorporated by reference. For a presentation of nucleotide sequence substitutions, such as codon preferences, see Ausubel et al, supra, at §§ A.1.1–A.1.24, and Sambrook et al, *Current Protocols in Molecular Biology*, Interscience N.Y. §§6.3 and 6.4 (1987, 1992), at Appendices C and D.

Preferred changes for analogs in accordance with the present invention are what are known as "conservative" substitutions. Conservative amino acid substitutions of those in the chimeric protein having essentially the naturally-occurring sIL-6R and IL-6 sequences, may include synonymous amino acids within a group which have sufficiently similar physicochemical properties that substitution between members of the group will preserve the biological function of the molecule, Grantham, *Science, Vol.* 185, pp. 862–864 (1974). It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues, Anfinsen, "Principles That Govern The Folding of Protein Chains", *Science*, Vol. 181, pp. 223–230 (1973). Analogs produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |

TABLE I-continued

Preferred Groups of Synonymous Amino Acids

| Amino Acid | Synonymous Group |
|---|---|
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Trp |

Examples of production of amino acid substitutions in proteins which can be used for obtaining analogs of the chimeric protein for use in the present invention include any known method steps, such as presented in U.S. Pat. RE 33,653, 4,959,314, 4,588,585 and 4,737,462, to Mark et al; U.S. Pat. No. 5,116,943 to Koths et al., U.S. Pat. No. 4,965,195 to Namen et al; U.S. Pat. No. 4,879,111 to Chong et al; and U.S. Pat. No. 5,017,691 to Lee et al; and lysine substituted proteins presented in U.S. Pat. No. 4,904,584 (Shaw et al).

In another preferred embodiment of the present invention, any analog of the chimeric protein for use in the present invention has an amino acid sequence essentially corresponding to that of the above noted basic chimeric protein of the invention. The term "essentially corresponding to" is intended to comprehend analogs with minor changes to the sequence of the basic chimeric protein which do not affect the basic characteristics thereof, particularly insofar as its ability to inhibit cancer cell proliferation or promote bone marrow transplantations, for example, is concerned. The type of changes which are generally considered to fall within the "essentially corresponding to" language are those which would result from conventional mutagenesis techniques of the DNA encoding the chimeric protein of the invention, resulting in a few minor modifications, and screening for the desired activity in the manner discussed above.

Analogs in accordance with the present invention include those encoded by a nucleic acid, such as DNA or RNA, which hybridizes to DNA or RNA under stringent conditions and which encodes a chimeric protein in accordance with the present invention, comprising essentially all of the naturally-occurring sequences encoding sIL-6R and IL-6. For example, such a hybridizing DNA or RNA may be one encoding the same protein of the invention having, for example, the sequence set forth in FIG. 3, but which differs in its nucleotide sequence from the naturally-derived nucleotide sequence by virtue of the degeneracy of the genetic code, i.e., a somewhat different nucleic acid sequence may still code for the same amino acid sequence, due to this degeneracy. Further, as also noted above, the amount of amino acid changes (deletions, additions, substitutions) is limited to up to about 30 amino acids, such that even with the maximum amount of changes, analogs in accordance with the present invention will be those which essentially retain the leader sequence (before processing), Ig-like domain, cytokine receptor N- and C-domains and receptor pre-membrane region (the region between the C-domain and the transmembranal domain) in the sIL-6R moiety and essentially all of the IL-6 moiety. Such nucleic acid would be a prime candidate to determine whether it encodes a polypeptide which retains the functional activity of the chimeric protein of the present invention. The term "stringent conditions" refers to hybridization and subsequent washing conditions which those of ordinary skill in the art conventionally refer to as "stringent". See Ausubel et al., *Current Protocols in Molecular Biology*, supra, Interscience, N.Y., para. 6.3 and 6.4 (1987, 1992), and Sambrook et al., supra. Without limitation, examples of stringent conditions include washing conditions 12–20° C. below the calculated Tm of the hybrid under study in, e.g. 2×SSC and 0.5% SDS for 5 minutes, 2×SSC and 0.1% SDS for 15 minutes; 0.1×SSC and 0.5% SDS at 37° C. for 30–60 minutes and then a 0.1×SSC and 0.5% SDS at 68° C. for 30–60 minutes. Those of ordinary skill in this art understand that stringency conditions also depend on the length of the DNA sequences, oligonucleotide probes (such as 10–40 bases) or mixed oligonucleotide probes. If mixed probes are used, it is preferable to use tetramethyl ammonium chloride (TMAC) instead of SSC. See *Ausubel*, supra.

The term "salts" herein refers to both salts of carboxyl groups and to acid addition salts of amino groups of the chimeric protein of the invention or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Of course, any such salts must have substantially similar activity to the chimeric protein of the invention or its analogs.

The present invention also concerns DNA sequences encoding the above chimeric protein of the invention and its analogs, as well as DNA vectors carrying such DNA sequences for expression in suitable mammalian, preferably human, cells. An embodiment of a vector of the invention is a plasmid pcDNA sIL-6R/IL-6 comprising the pcDNA3 vector (Invitrogen) containing the sIL-6R/IL-6 fused sequences under the control of a cytomegalovirus (CMV) promoter.

The present invention also concerns transformed mammalian, preferably human, cells capable of expressing the above proteins of the present invention. An embodiment of such transformed cells are human embryonal kidney cells 293 (HEK 293, ATCC CRL 1573) transfected by pcDNA sIL-6R/IL-6 which secrete the fused sIL-6R/IL-6 chimeric as a 85 kDa glycoprotein.

A further embodiment is plasmid pcDNA sIL-6R/L/IL-6 which differs from the above pcDNA sIL-6R/IL-6 by insertion in the EcoRI site of short linkers encoding 10 additional aminoacids. A number of different sequences, of various lengths, can be introduced to optimize the distance between sIL-6R and IL-6.

The invention also includes a chimeric protein in which the IL-6 moiety precedes the sIL-6R (as in FIG. 11).

The present invention further concerns a method for producing and purifying the chimeric protein of the invention or its analogs which comprises growing the above transformed cells under conditions suitable for expression and secretion of the chimeric protein product into the culture medium and then purifying the secreted protein by immunoaffinity chromatography using anti-sIL-6R monoclonal antibodies 34.4 as noted in Example 2 and 5 below.

The invention also concerns a pharmaceutical composition comprising as active ingredient an sIL-6R/IL-6 chimera or analogs thereof or mixtures thereof or salts thereof and a pharmaceutically acceptable carrier, diluent or excipient. An embodiment of the pharmaceutical composition of the invention includes a pharmaceutical composition for enhanced IL-6 type action, for the treatment of cancers, for bone marrow transplantation, for increase of hematopoiesis, in particular thrombopoiesis, for treatment of neurological conditions, for the treatment of liver disorders, and other applications of IL-6 or related cytokines.

The pharmaceutical compositions of the invention are prepared for administration by mixing the chimeric protein, or its analogs with physiologically acceptable carriers, and/or stabilizers and/or excipients, and prepared in dosage form, e.g., by lyophilization in dosage vials. The method of administration can be via any of the accepted modes of administration for similar agents and will depend on the condition to be treated, e.g., intravenously, intramuscularly, subcutaneously, by local injection or topical application, or continuously by infusion, etc. The amount of active compound to be administered will depend on the route of administration, the disease to be treated and the condition of the patient. Local injection, for instance, will require a lower amount of the protein on a body weight basis than will intravenous infusion.

The present invention also concerns uses of the chimeric protein of the invention or its analogs or mixtures thereof for the treatment of cancers, for bone marrow transplantations, for increasing hematopoiesis, especially thrombopoeisis, for treatment of neurological conditions, for protection of liver tissues in patients with necrotic diseases due to chemicals (e.g. carbon tetrachloride, alcohol, paracetamol) or other causes (e.g. viral, surgical) and for use in other applications of IL-6 or related cytokines. Likewise, the present invention also concerns the chimeric protein or analogs thereof or mixtures thereof for use in the preparation of medicaments for treating the above-mentioned ailments or for use in the above noted indications.

In addition to the above mentioned methods of treatment, also ex-vivo procedures and gene therapy with the chimera and or DNA encoding it are contemplated.

The present invention will now be described in more detail in the following non-limiting Examples and the accompanying drawings.

EXAMPLE 1

Construction of the sIL-6RδVal/IL-6 Chimera Expression Vector

Figure 1B:
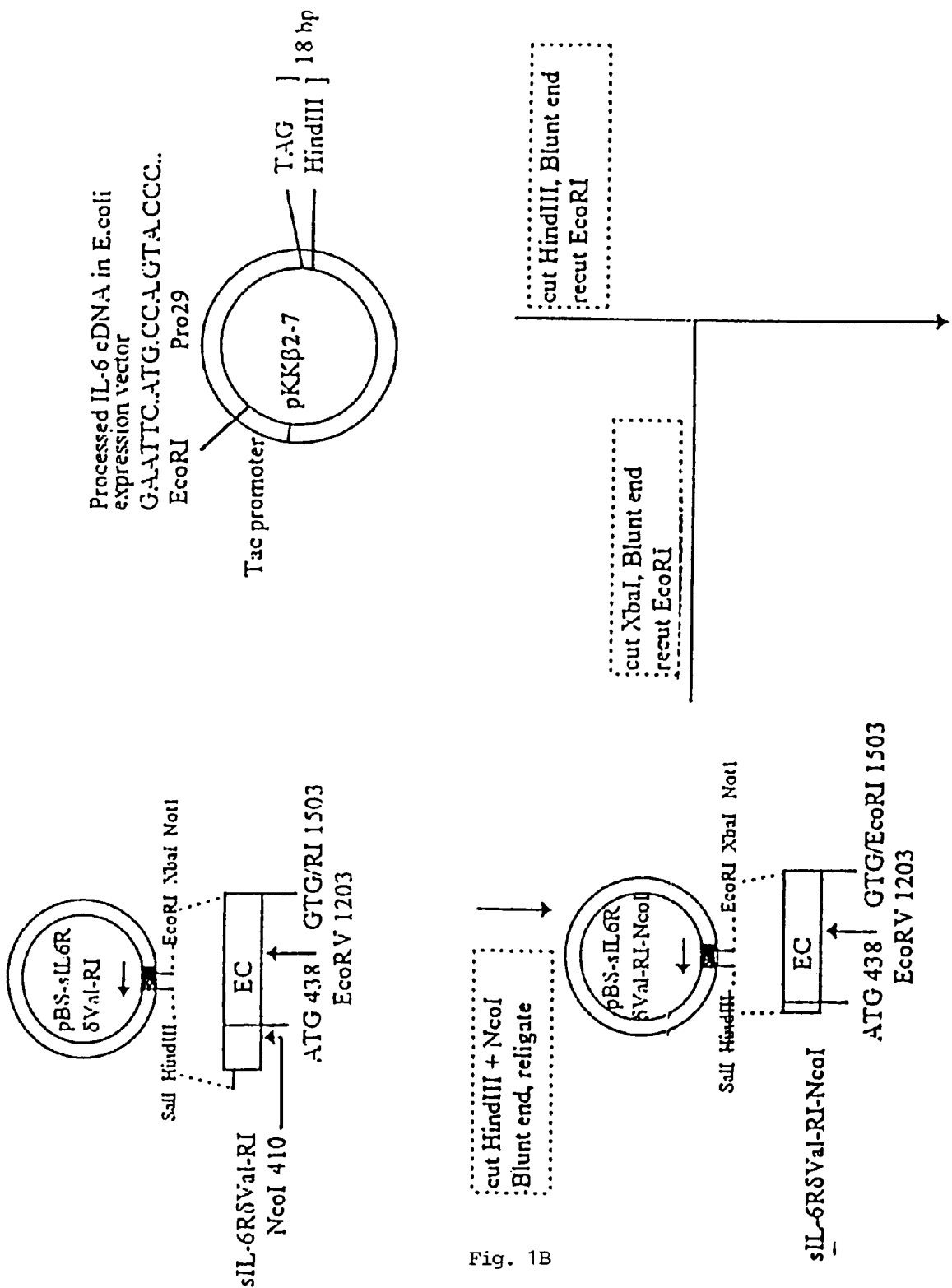
FIG. 1 (A, B, C) depicts a schematic representation of the various vectors, reagents and process steps used in the construction of the chimeric DNA molecule encoding a chimeric protein in which is conserved the structure of the natural form of sIL-6R ending at the Val 356 residue followed by the sequence of the natural, mature, processed form of IL-6 as detailed in Example 1.
Figure 1C:
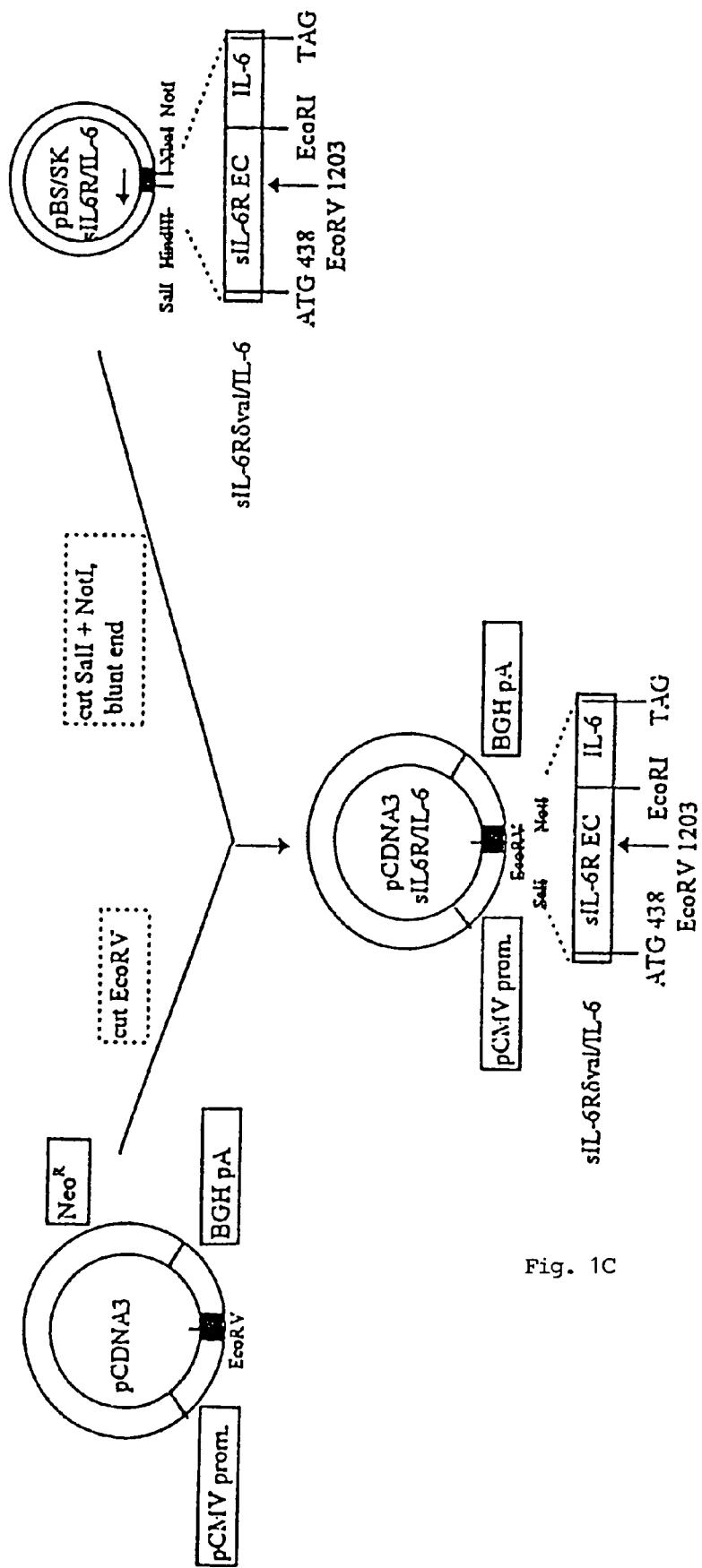

In FIG. 1, there is shown a schematic flow-diagram of the steps taken to construct the expression vector carrying the sequence coding for the sIL-6RδVal/IL-6 chimeric protein, inclusive of all the various starting and intermediary vectors, various reagents and reaction steps. This construction procedure was essentially using techniques well known in the art for constructing expression vectors of choice (see, for example, Sambrook et al., 1989). The procedure was, briefly, as follows:

A library of cDNAs from human breast carcinoma T47D cells was cloned in the lamda (λ) gt11 bacteriophage and screened with oligonucleotide probes derived from the IL-6R sequence of Yamasaki et al (1988). One λgt11 cDNA clone was isolated which had the entire human IL-6R coding sequence. The insert was excised from λgt11 by EcoRI and cloned in the Multiple Cloning Site (MCS) of the E. coli phagemid Blue Script pBS/SK (Stratagene Cloning Systems, LaJolla, Calif.). This plasmid pBS/SK-IL-6R (FIG. 1) was cut by EcoRI which was then blunt-ended and recut with EcoRV to isolate the 5' fragment of IL-6R of 959 base pairs (bp) ending at the EcoRV site of IL-6R (coordinate 1203). This fragment extracted from an agarose gel electrophoresis was cloned in a new pBS/SK vector opened at the EcoRV of the MCS (pBS/SK-sIL-6R-RV in FIG. 1).

The above noted, previously obtained pBS/SK-IL-6R DNA was subjected to Polymerase Chain Reaction (PCR) to amplify a 368 bp fragment between the forward primer 1137–1156 and the reverse primer 1505–1488. The reverse primer was synthesized with an EcoRI site immediately following the codon for Valine-356 of the IL-6R (see FIG. 1), since this Valine residue was previously determined to be the carboxy-terminal amino acid of the natural form of the soluble sIL-6R excreted in human urine (Novick et al, 1990; Oh et al, 1996; co-owned U.S. Pat. No. 5,216,128 and EP Pat. No. EP 413908 B1). The PCR product was cut by EcoRV and by EcoRI and ligated into pBS/SK-sIL-6R-RV between the EcoRV site of IL-6R and the EcoRI site of the MCS (FIG. 1). The resulting plasmid pBS-sIL-6RδVal-RI was then shortened to remove 5' untranslated sequences by ligation of the HindIII site of MCS with the NcoI site at base pair 410 of IL-6R (both sites being first blunt-ended), to yield pBS-sIL-6RδVal-RI-NcoI (FIG. 1).

The IL-6 sequence was derived from plasmid pKKβ2-7 which, as previously described (Chen et al, 1988), was constructed by insertion of the BstNI-cut IFN-β2/IL-6 cDNA (Zilberstein et al, 1986) into the EcoRI site of the E. coli expression vector pKK223-3 (Pharmacia, Uppsala, Sweden) using a synthetic oligonucleotide with an EcoRI site followed by a Methionine codon and the codon for Proline-29 of IL-6 and ending at a BstNI (EcoRII) site. The IL-6 cDNA insert of pKKβ2-7 ends 7 base pairs after the termination codon in a NlaIV site and is followed 11 bp later by the HindIII site of the pKK223-3 vector (FIG. 1). The pKKβ2-7 DNA was cut with HindIII, blunt-ended and recut with EcoRI and the IL-6 cDNA inserted into pBS-sIL-6R-δVal-RI-NcoI so as to fuse the mature sequence of IL-6 (starting at Proline-29) immediately after Valine-356 of the IL-6R and separated by only 3 codons (Glu-Phe-Met). The resulting plasmid pBS/SK-sIL-6R/IL-6 (FIG. 1) was then recut at the SalI and NotI sites of its MCS and the insert was cloned into the EcoRV site of pcDNA3 (Invitrogen Corporation, San Diego, Calif.). The resulting plasmid pCDNA3-sIL-6R/IL-6 (FIG. 1) contains the insert downstream of the strong cytomegalovirus (CMV) promoter and followed by a polyadenylation site insuring efficient transcription of the sIL-6RδVal/IL-6 chimera. The conservation of the 5'end of the sIL-6R in the chimera ensures that upon expression in mammalian cells the signal peptide function and processing of the N-terminus of the chimeric protein will be as in the natural sIL-6R.

As indicated above, an advantageous characteristic of the sIL-6RδVal/IL-6 construct is that it is essentially the fusion of the natural form of sIL-6R and of the natural form of IL-6 as they exist in the human body, and without extraneous polypeptide sequences. However, the conservation of the EcoRI site in the sIL-6RδVal/IL-6 construct (FIG. 1) allows to easily introduce linker polypeptide segments between the sIL-6R and the IL-6 moieties. One such construct with the β-amino acid linker sequence Glu-Phe-Gly-Ala-Gly-Leu-Val-Leu-Gly-Gly-Gln-Phe-Met (SEQ ID NO:1) introduced between Val-356 of sIL-6R and Pro-29 of IL-6, was also constructed (sIL-6RδVal/L/IL-6) (SEQ ID NO:13).

EXAMPLE 2

Expression of the sIL-6RδVal/IL-6 Chimera in Human Cells

Using essentially standard techniques of mammalian cell culture, cell transfection and analysis of the transfected cells for expression of the newly introduced DNA sequence to be expressed (for procedures, see, for example, Sambrook et al., 1989), the above plasmid construct (Example 1) was used to transfect human cells and its expression therein was assessed. Briefly, the following procedures were employed:

Human HEK 293 cells (ATCC CRL 1573, transformed primary human embryonal kidney cells) were transfected with the plasmic construct pCDNA3-sIL-6R/IL-6 DNA (set forth in Example 1 above). Log phase cultures of HEK 293 were trypsinized and seeded in 9 cm Nunc plates ($2.5 \times 10^6$ cells/plate). One day later, transfection was carried out with 10 μg pCDNA3-sIL-6R/IL-6 DNA by the $CaPO_4$ precipitation procedure (Sambrook et al, 1989) and 1 hour later the medium changed to DMEM-10% FCS and the culture continued for an additional 16 hours. After changing the medium to DMEM-2% FCS, the secreted proteins were collected for two consecutive periods of 48 hours. Debris was removed by centrifugation at 1,000 rpm for 10 minutes and the supernatant tested by an ELISA for sIL-6R using polyclonal rabbit anti-sIL-6R and mouse McAB 17.6 (Novick et al, 1991). A concentration of 1.2 μg/ml sIL-6R-equivalents was found, indicative of very efficient expression of the chimeric sIL-6R/IL-6 protein in the transfected human cells.

Immunopurification of the secreted chimeric protein (sIL-6R/IL-6) was carried out with Monoclonal Antibody 34.4 specific to an epitope in the extracellular domain of human sIL-6R (Novick et al, 1991; Halimi et al, 1995). The 34.4 hybridoma cells were grown in the peritoneal cavity of mice and the immunoglobulin (Ig) fraction was obtained from the ascitis fluid by ammonium sulfate precipitation. Affigel-10 (Bio-Rad Labs, Richmond, Calif.) was used to immobilize McAB 34.4 (15 mg Ig coupled to 1 ml Affigel-10). The supernatants containing the secreted proteins from the HEK 293 cells transfected by pCDNA3-sIL-6R/IL-6 were adsorbed on columns of McAB 34.4 (0.3 ml column for 15 ml supernatant). After washing with PBS, the bound proteins were eluted by 25 mM citric acid pH 2.5, then immediately neutralized by 1 M Hepes buffer pH 8.5 and dialyzed overnight (about 8–12 hrs) against PBS.

Figure 2A:
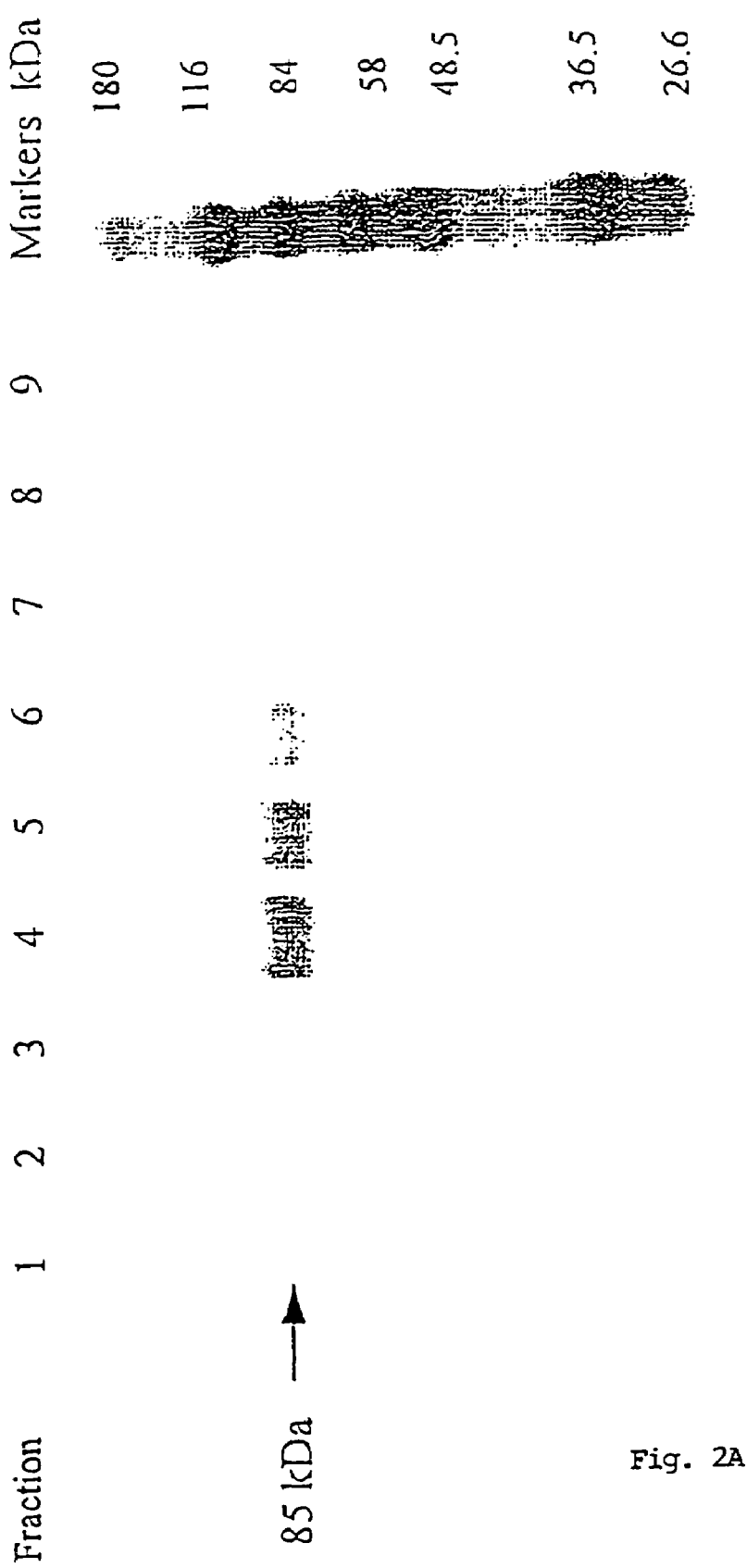
FIG. 2 (A,B) shows thy results obtained from the analysis performed to identify the sIL-6RδVal/IL-6 p86 chimera by polyacrylamide gel electrophoresis (A) and by bioactivity profile (B), wherein in FIG. 2A there is shown a reproduction of a Coomassie stained gel on which were electrophoresed immunopurified fractions eluted from affinity chromatography columns loaded with a secreted protein sample obtained from cell cultures transfected with a vector encoding the chimeric protein; and in FIG. 2B there is shown a graphic representation of the biological activity (growth inhibition of F10.9 melanoma cells) of each of the above noted fractions eluted from the affinity chromatography columns, all as detailed in Examples 2 and 3.
Figure 2B:
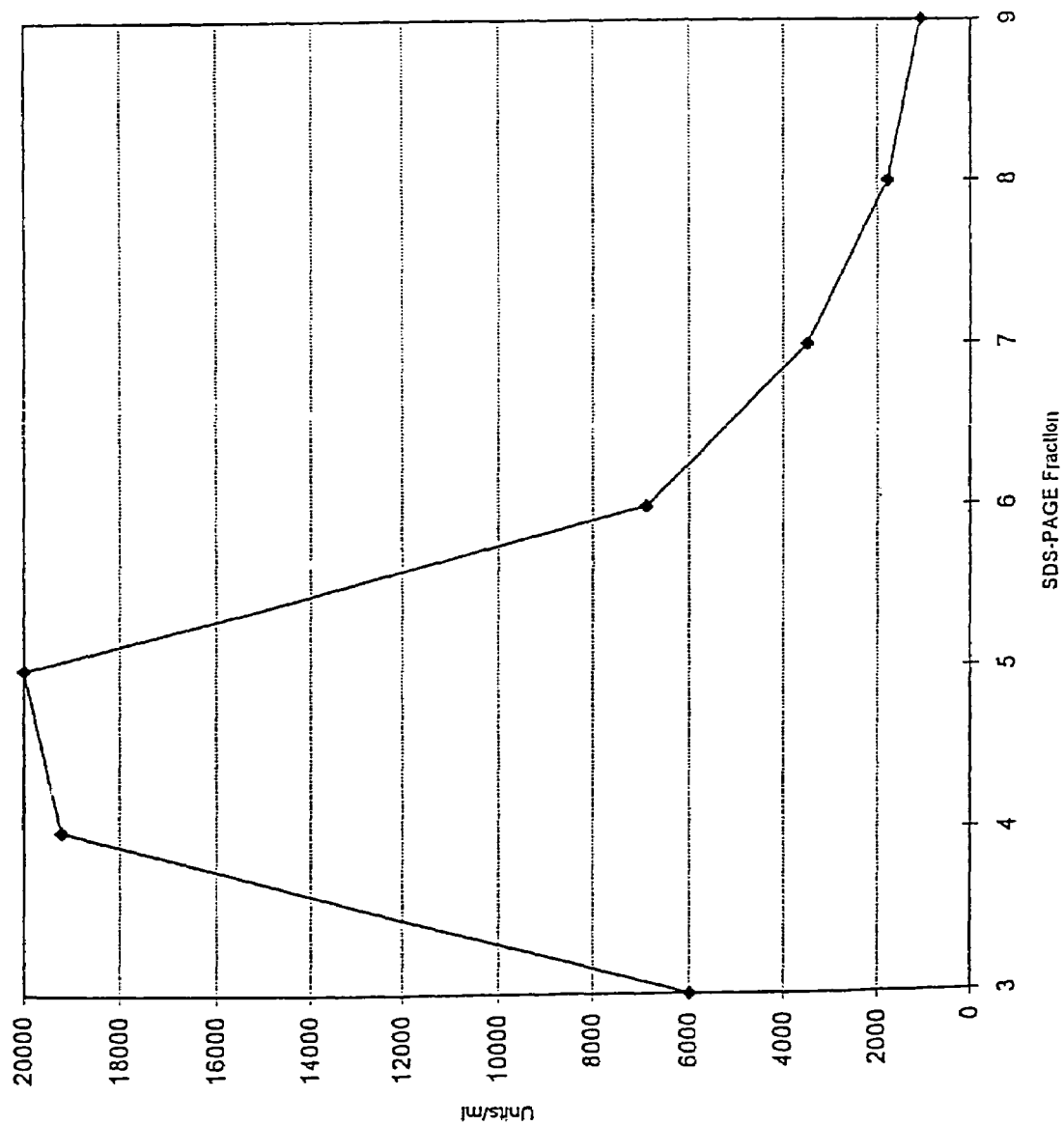

Analysis of the immunopurified protein by polyacrylamide gel electrophoresis in SDS showed a unique protein band stained by Coomassie blue (FIG. 2). The molecular weight of the protein was 85 kilodaltons as expected from the fusion of the glycosylated forms of sIL-6RδVal (60 kDa as shown in Oh et al, 1996) and glycosylated IL-6 (23–26 kDa as shown in Zilberstein et al, 1986). The aminoacid sequence of the sIL-6R/IL-6 is 543 aminoacids, which after processing of the signal peptides would predict a protein of 524 aminoacids or about 58 kDa (FIG. 3). The much larger size of the sIL-6R/IL-6 chimera produced from the recombinant DNA in human cells indicates that glycosylation accounts for a sizable portion of the molecule.

EXAMPLE 3

Figure 4:
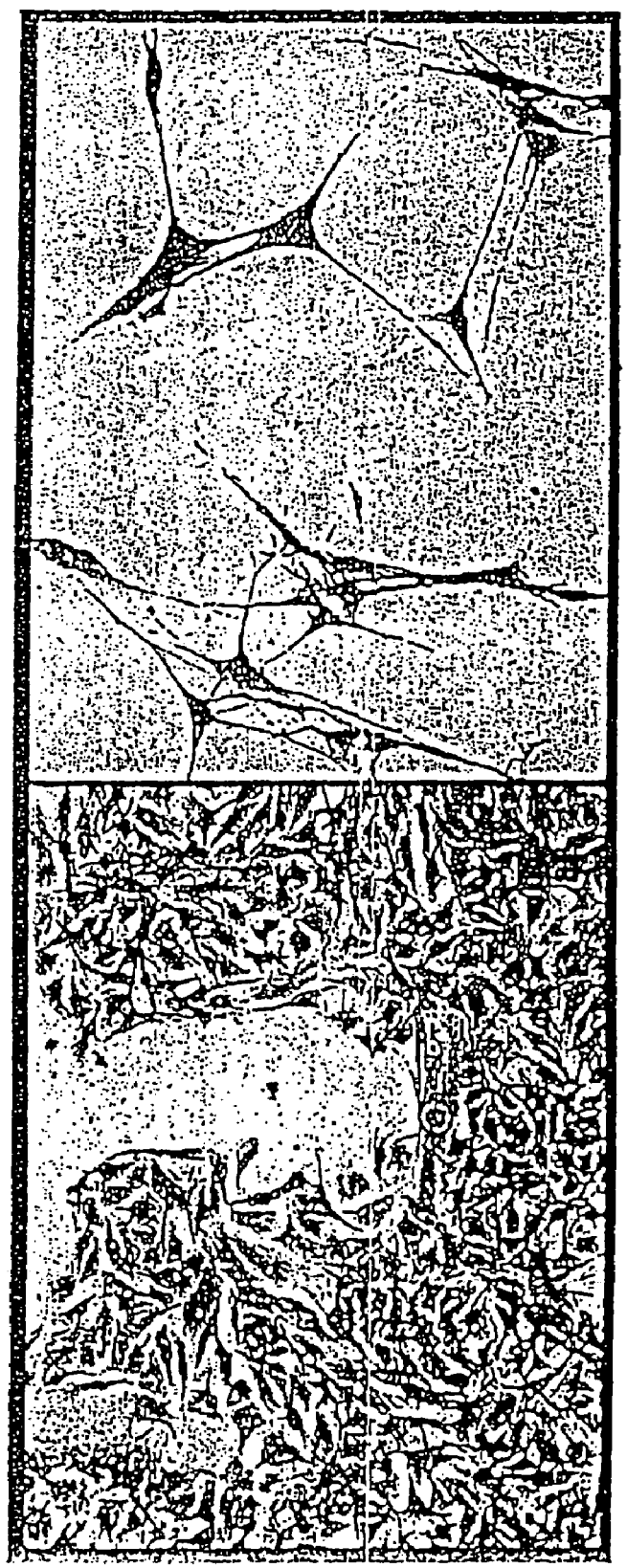
FIG. 4 (A, B) shows photographs of F10.9 melanoma cells in culture W without (A) and with (B) treatment with the sIL-6R/IL-6 chimeric protein for 4 days, wherein in FIG. 4B there is apparent the morphological changes induced in such metastatic melanoma cells (F10.9 cells) by treatment with the sIL-6R/IL-6 chimera, as described in Example 3.

The sIL-6R/IL-6 Chimera Arrests Growth and Induces Differentiation of Metastatic Melanoma Cells The F10.9 clone derived from B16 melanoma cells forms highly metastatic tumors in C57Black/6 mice which kill the animals from pulmonary metastases within 2–3 months (Katz et al, 1995). Addition of the sIL-6R/IL-6 chimeric protein to F10.9 cells culture produces a profound morphological change in the cells and an arrest in their growth (FIG. 4). The F10.9 cells treated by the chimera become elongated, with protruding dendritic extensions, resembling the spindloid differentiation of embryonic melanocytes or glial cells.

Figure 5:
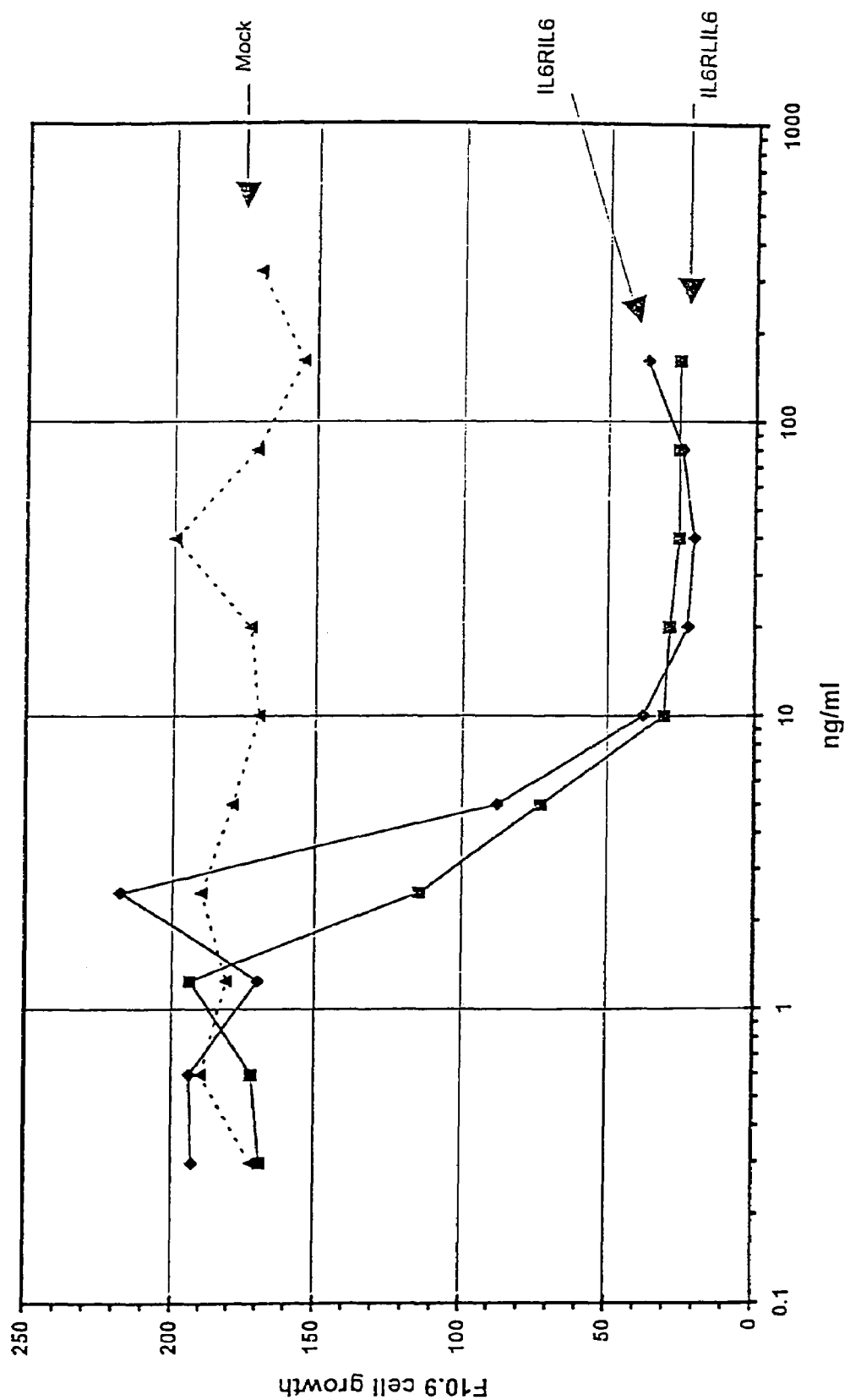
FIG. 5 is a graphic representation of the results depicting the growth inhibition of F10.9 melanoma cells by the sIL-6R/IL-6 chimeric protein at various concentrations of the chimera ranging from about 0.12 ng/ml to about 150 ng/ml, where the chimera with only 3 amino acid linker IL-6RIL-6 as described in Example 3 is compared to a chimera with a long 13 amino acid linker (IL-6RLIL-6)
Figure 6:
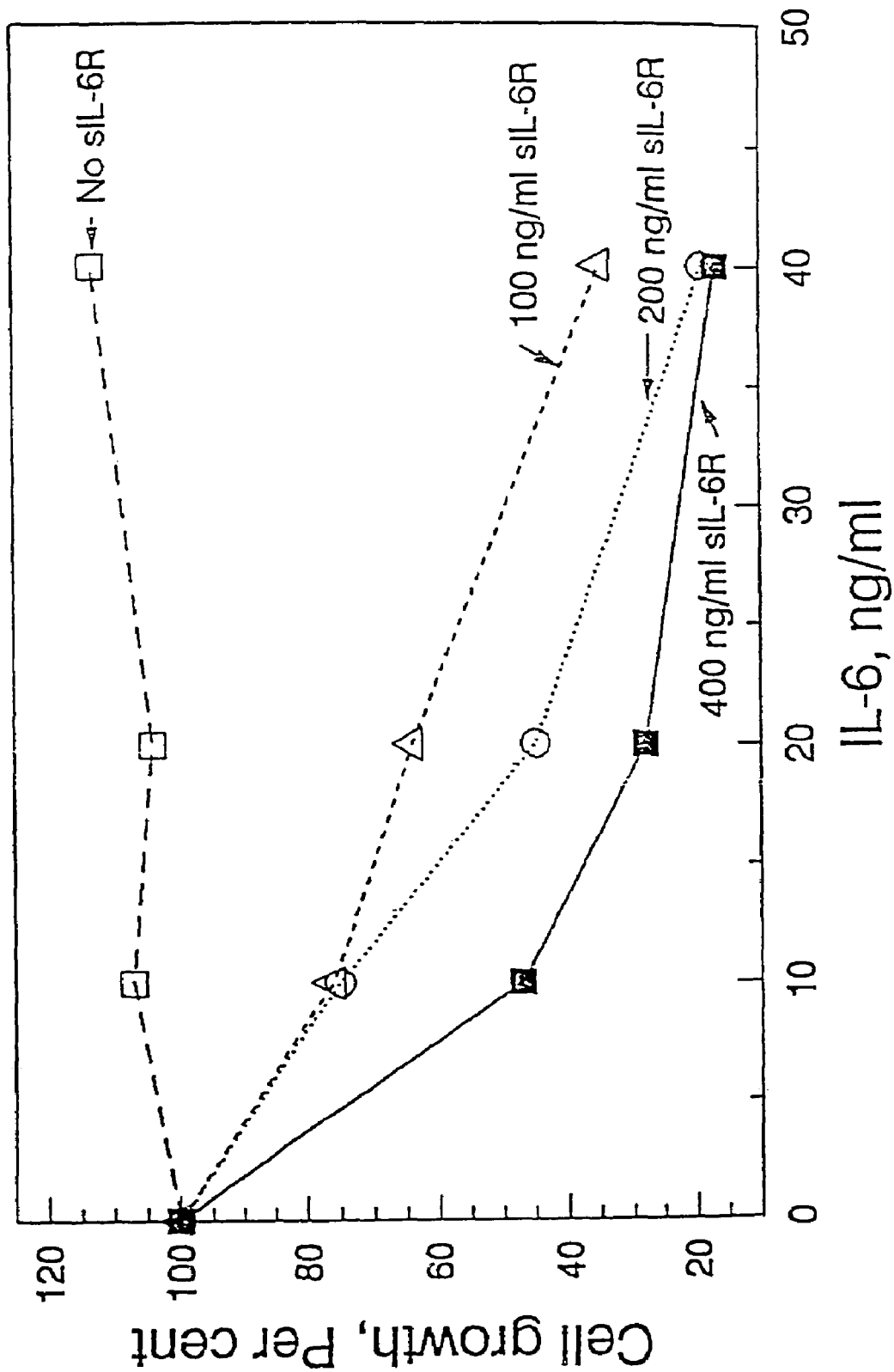
FIG. 6 is a graphic representation of the results depicting the absence of growth-inhibitory effects on F10.9 melanoma cells of either isolated IL-6 alone (dotted upper curve with open squares) at concentrations ranging from 0–40 ng/ml of IL-6 and sIL-6R alone (point of convergence of all curves on vertical axis where IL-6 concentration is zero); as well as the observed growth inhibitory effects when IL-6 and sIL-6R are added together at various concentrations of each wherein the IL-6 concentration ranges from 10 ng/ml to 40 ng/ml, and sIL-6R added at three concentrations of 100 ng/ml, 200 ng/ml and 400 ng/ml for each IL-6 concentration, as illustrated in the three lower curves (two dotted curves with open triangles and circles and full curve with closed squares), as described in Example 3.

The growth of the cells was quantitated 4 days after seeding $3 \times 10^3$ cells in wells of a 96-well microplate in 0.2 ml RPMI 1640 medium with 10% FCS. The cells were fixed in 12.5% glutaraldehyde for 30 minutes, washed in water and stained with 0.1% crystal violet for 30 minutes. After thorough washing and drying, the stain was extracted by 10% acetic acid and the optical density determined at 540 nm. The chimera produced a dose-dependent inhibition of growth with a complete growth inhibition at concentrations as low as 10 ng/ml of the chimeric (p85) protein (FIG. 5). Both chimeric proteins sIL-6RδVal/IL-6 and sIL-6RδVal/L/IL-6 (chimera with the longer linker between the sIL-6R and IL-6 moieties, see Example 1) were similarly active. This result also serves to show that the linker peptide between the sIL-6R and IL-6 moieties in the chimera, is not essential for the activity of the chimera as the above sIL-6RδVal/IL-6 chimera has only a very short 3 amino acid linker while the above sIL-6RδVal/L/II-6 has a longer 13 amino acid linker peptide, but both have essentially the same activity in inhibiting the growth of the metastatic cells. In contrast, neither IL-6 alone, nor the sIL-6R δVal alone inhibit the growth of these melanoma cells (FIG. 6) demonstrating the unique activity of the sIL-6R/IL-6 (p85) chimeric protein. To obtain a similar effect, a mixture of 200–400 ng/ml IL-6 and 125 ng/ml sIL-6RδVal is required (FIG. 6). When calculated in molar concentrations, the maximal inhibition of F10.9 cells required 7.5 nM IL-6 and 2 nM sIL-6RδVal versus only 0.12 nM of the sIL-6R/IL-6 chimera.

The growth inhibitory activity of the p85 sIL-6R/IL-6 chimeric protein was followed during the immunopurification on McAB 34.4 columns (see Example 2). The pattern of activity corresponded to the intensity of the p85 band seen in the different fractions of the SDS polyacrylamide gel electrophoresis in FIG. 2.

EXAMPLE 4

The sIL-6R/IL-6 Chimera is Essential for Engraftment of Human Bone Marrow Transplanted Cells Engraftment of hematopoietic stem cells from human bone marrow can be studied after transplantation into severe combined immunodeficient (SCID) mice (Vormoor et al, 1994). SCID-NOD mice were subjected to sublethal irradiation and injected in the tail vein with $3 \times 10^5$ human $CD34^+$ bone marrow cells. Prior to injection, the purified $CD34^+$ cells were maintained for 3 days in liquid cultures with different combinations of cytokines. After one month, the mice were sacrificed and bones were taken to collect the bone marrow cells. The engraftment of human cells in the SCID-NOD recipient mice was evaluated by Southern blot hybridization to human repetitive DNA.

Figure 7:
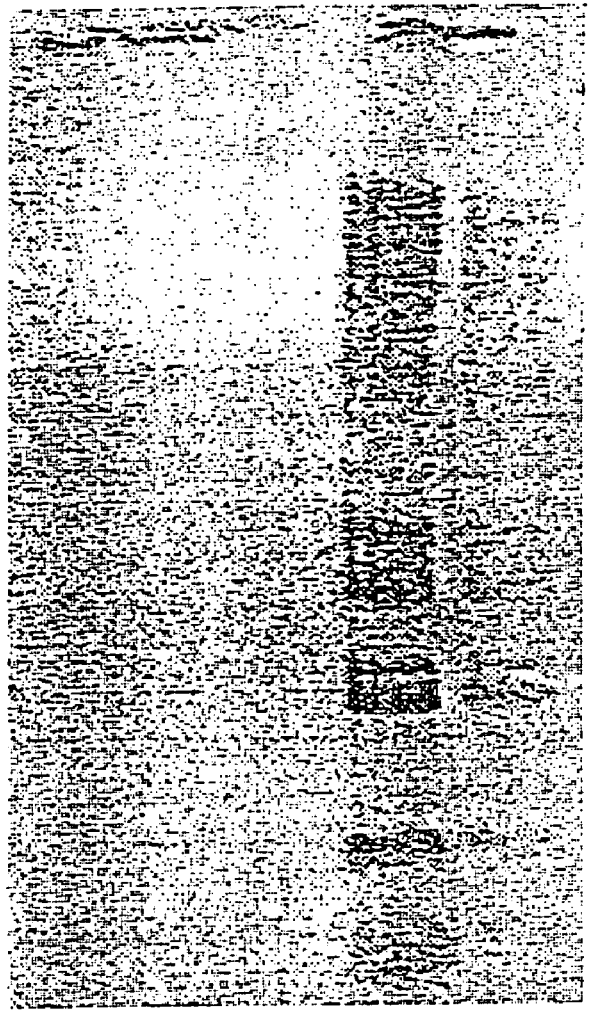
FIG. 7 is a reproduction of an autoradiogram of a Southern blot showing the requirement of the sIL-6R/IL-6 chimeric protein for successful engraftment of human hematopoietic stem cells during bone marrow transplantation in SCID-NOD mice (two right hand lanes representing the mice which received the sIL-6R/IL-6 chimeric protein in addition to the other necessary factors, SCF, FLT-3, and this in contrast to the three left hand lanes which represent mice having received only SCF and FLT-3 and SCF, FLT-3 as well as isolated, i.e. non-fused, IL-6 and sIL-6R), as described in Example 4.

Stem-cell factor (SCF, steel factor or ckit-ligand) and Flt3-ligand (flt3/flk2 tyrosine kinase receptor ligand) have been found important for survival and proliferation of the most primitive pluripotential hematopoietic stem cells capable of long-term engrafment in recipient bone marrow (McKenna et al, 1995). As seen in FIG. 7, these two factors by themselves were insufficient to promote the engraftment of human cells in the bone marrow of the SCID-NOD recipient mice. Addition of the sIL-6R/IL-6 chimeric protein was required for engraftment to be detected at significant levels. At 100 ng/ml, the sIL-6R/IL-6 chimera was much more active than the isolated IL-6 (50–200 ng/ml) and sIL-6R (125–1250 ng/ml) (FIG. 7). The requirement for the sIL-6R/IL-6 chimera indicates that this protein is essential for the survival and proliferation of the non-committed pluripotential hematopoietic stem cells which can home into and repopulate the bone marrow environment, indicating that this protein may be useful in bone marrow transplantation clinical protocols.

This is the first demonstration that the sIL-6R/IL-6 chimera has the following at least two newly found activities:

(i) When added together with both of the factors SCF and Flt3-ligand to human hematopoietic primitive progenital cells, it promotes their survival and proliferation; and (ii) It is active (and apparently essential) in an in vivo model of a human bone marrow transplantation in immunodeficient mice.

EXAMPLE 5

The sIL-6R/IL-6 chimera is Active on Highly Purified Primitive Hematopoietic Stem Cells Human cord blood mononuclear cells were subjected to fractionation of low density mononuclear cells (NMC) on Ficoll-Paque (Pharmacia Biotech, Uppsala, Sweden) followed by a mini MACS kit (Miltney Biotec, Bergisch Gladbach, Germany) to prepare a 80% pure population of $CD34^+$ cells. These cells were then passed over immobilized anti-CD38 monoclonal antibody or sorted by fluorescence activated cell sorting and the $CD34^+CD38^-$ population, corresponding to about 0.1% of the original cells, was recovered. These purified stem cells (20,000 cells) were placed in suspension cultures in 0.5 ml RPMI medium, 10% fetal calf serum (FCS), 1% bovine serum albumin containing 50 ng/ml stem cell factor (SCF) and 100 ng/ml flt3-ligang (FL) (both from R&D Systems, Minneapolis, Minn.). Half of the cultures were supplemented with 100 ng/ml sIL-6R/IL-6 chimera, the others were cultured without. Incubation was at 37° C. in 5% $CO_2$, for 6 days. The number of bone marrow repopulating cells was evaluated by injection (i.v.) of all the cells from these in vitro cultures into sub-lethally irradiated NOD-SCID mouse. The mice were maintained in germ-free conditions. After 6 weeks, the mice were sacrificed and the marrow of their long bones was recovered. These bone marrow (BM) cells were plated on semi-solid 0.9% methylcellulose plates with 30% FCS, 50 μM β-mercaptoethanol, 50 ng/ml SCF, 5 ng/ml IL-3, 5 ng/ml GM-CSF, 6 u/ml erythropoietin (all R&D Systems). The cultures contained also human serum, conditions which prevent growth of mouse colonies. The results (Table IV) indicated that the sIL-6R/IL-6 chimera addition to the suspension cultures produces a 30–50 fold increase in the number of human colony forming cells (CFU) recovered from the transplanted mice as compared to SCF and FL alone. This represents a large increase in the number of SCID-repopulating stem cells present in the suspension cultures at day 6 compared to day 0. In the absence of sIL-6R/IL-6 chimera, SCF and FL produced no increase in the number of stem cells during the 6 days of suspension culture. The DNA of the BM cells recovered from the transplanted NOD/SCID mice was analyzed by Southern blot as in Example 4. The amount of human DNA recovered was 10 times higher when the mice received the cells cultured with chimera as compared to without chimera.

The CFU progenitors from bone marrow of NOD/SCID mice as in Table IV, gave rise to hematopoietic cells of different myeloid lineages (macrophage and granulocyte) as well as erythroid and lymphoid lineages (e.g. $CD19^+$, $CD56^+$) only when the human blood cells had been cultured with sIL-6R/IL-6 chimera prior to transplantation.

TABLE IV

Human stem cells capable of repopulating bone marrow of NOD/SCID mice

| Additions during the suspension culture of $CD34^+CD38^-$ human cells from Cord Blood | Days of culture | Number of human hematopoietic colonies formed from BM of transplanted NOD/SCID mice |
| --- | --- | --- |
|  | 0 | 4 |
| SCF + FL | 6 | 2–3 |
| SCF + FL + sIL-6R/IL-6 | 6 | 50–100 |

Additional experiments compared the effect of sIL-6R/IL-6 on the cord blood $CD34^+CD38^+$ population to those on the highly purified $CD34^+CD38^-$ stem cells. The in vitro expansion of the highly purified cells was much more strongly enhanced by sIL-6R/IL-6 than that of the less purified cells (Table V). This indicates that the most primitive stem cells are the preferential target of the sIL-6R/IL-6 effect on cell expansion.

TABLE V

In vitro Expansion of Hematopoietic Stem Cells

| Cell population seeded (20,000 cells) | Cell number at day 6 with SC + FL | Cell number at day 6 with SC + FL + sIL-6R/IL-6 |
| --- | --- | --- |
| Expt. 1 | | |
| $CD34^+CD38^+$ | 780,000 | 675,000 (x0.86) |
| $CD34^+CD38^-$ | 42,000 | 153,000 (x3.6) |
| Expt. 2 | | |
| $CD34^+CD38^+$ | 330,000 | 507,000 (x1.5) |
| $CD34^+CD38^-$ | 3,000 | 18,000 (x6.0) |

The in vitro maintenance of the Bone Marrow-repopulating activity was measured by increasing the length of the suspension of cultures of highly purified $CD34^+CD38^-$ stem cells before injection to the NOD/SCID mice. The engraftment was evaluated by the proportion of human DNA in the Bone Marrow of the recipient mice 6 weeks after i.v. injection of the cultured cells. When sIL-6R/IL-6 was added to SCF and FL during the cultures, a high engrafment (>1% human DNA) was still observed after two weeks of culture, and the engrafment was higher than in the non-cultured cells. In contrast thereto, experiments with cultures containing SCF, FL, GM-CSF, IL-3 have shown that no SCID-repopulating cells remain after one week of culture (Bhata, M. et al., J. Exp. Med. 186, 619–624, 1997).

These results show that sIL-6R/IL-6 allows to expand and maintain, human primitive stem cells capable of engraftment in recipient bone marrow. The stem cells remain active in a non-differentiated state while multiplying. The sIL-6R/IL-6 chimera provides a new means to culture engrafting hematopoietic cells. This may also allow to use retroviral vectors to introduce genes into engrafting stem cells, in protocols of gene therapy. Until now, this has not been possible with human stem cells because these primitive cells could not be maintained in vitro in a cycling state, as required for retroviral DNA integration. The sIL-6R/IL-6 chimera solves this problem.

EXAMPLE 6

Production of IL-6R/IL-6 Chimera in CHO Cells

DNA of plasmid sIL-6R/IL-6 pcDNA3 as in FIG. 1, was co-transfected into Chinese Hamster Ovary (CHO) cells, together with DNA of plasmid pDHFR as described in Mory et al (DNA 5, 181–193, 1986). Among the transfectants growing in 50 nM Methotrexate, clone L12-[IL-6R/IL-6] was isolated. This clone was found to be stable over many passages and semi-confluent cultures routinely secrete into the culture medium amounts of 2.5 μg/ml of the IL-6R/IL-6 chimera.

For purification of the IL-6R/IL-6 chimera, 3.25 liters of medium from clone L12 cultures in 2% bovine serum were concentrated to 200 ml. This was adsorbed on a 18 ml column of anti human sIL-6R Monoclonal Antibody 34.4 coupled to Affigel 10 beads and eluted as described (Novick et al., Hybridoma, 10, 137–146, 1991). A 25 mM citric acid eluate was immediately neutralized with 1 Hepes buffer pH 8.6. The proteins were concentrated on a 10 kDa cut-off Amicon membrane to a final concentration of 1 mg/ml. Upon SDS-PAGE, a single band of 85 kDa corresponding to the IL-6R/IL-6 chimera was observed. Glycosylation was demonstrated by size reduction after treatment with glycosidase (Boehringer, Mannheim). The biological activity of the CHO produced IL-6R/IL-6 chimera was found stable for at least 5 months at 4° C. Routinely, storage is at −70° C.

EXAMPLE 7

Affinity of IL-6R/IL-6 Chimera to gp130

Figure 8:
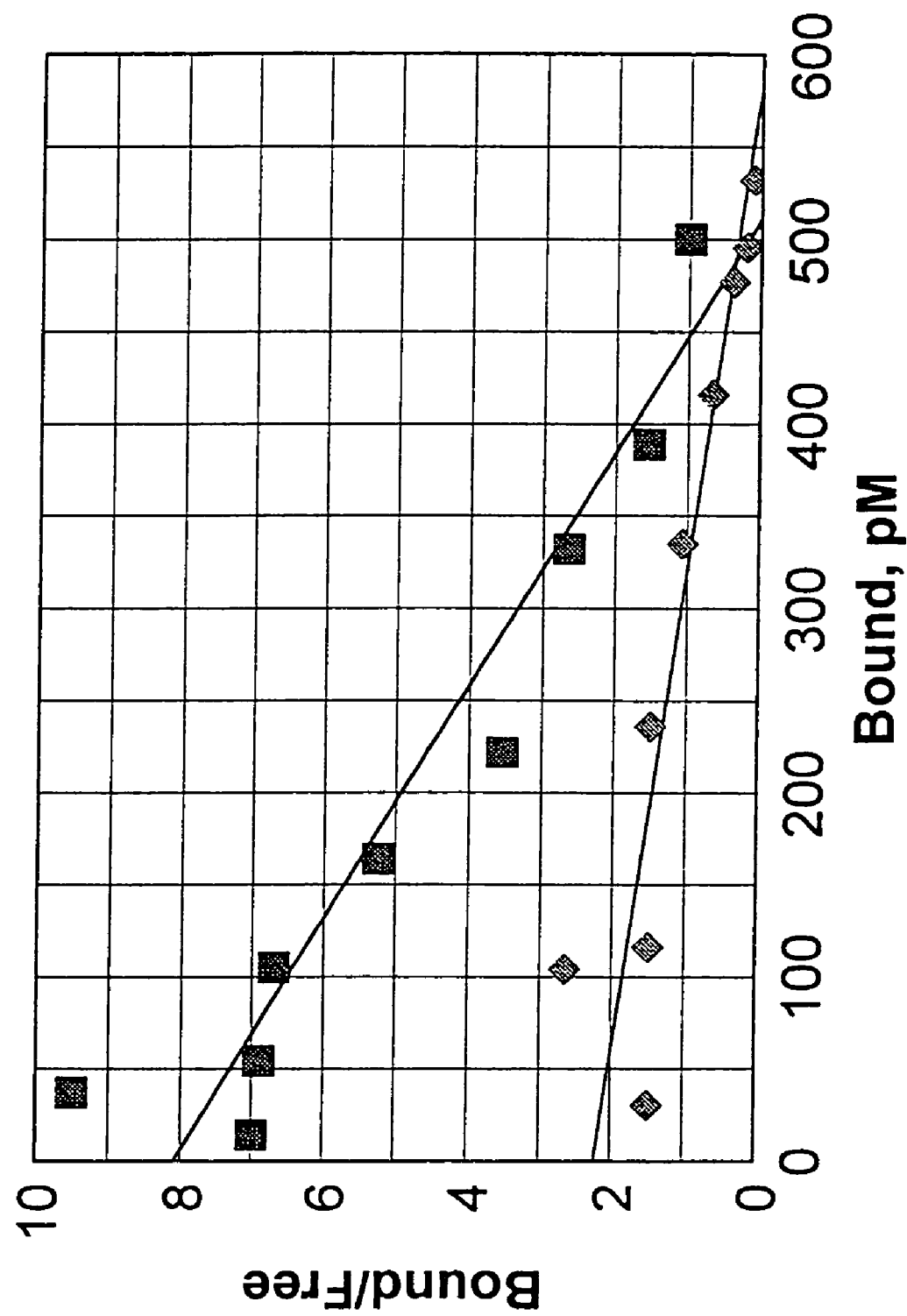
FIG. 8 is a Scatchard plot of the affinity characteristics of the sIL-6R/IL-6 chimera as compared to a mixture of IL-6 and sIL-6R, the values of the chimera depicted by filled squares and of the mixture by filled diamonds, the ratio of the slopes being 4 to 1.
Figure 9:
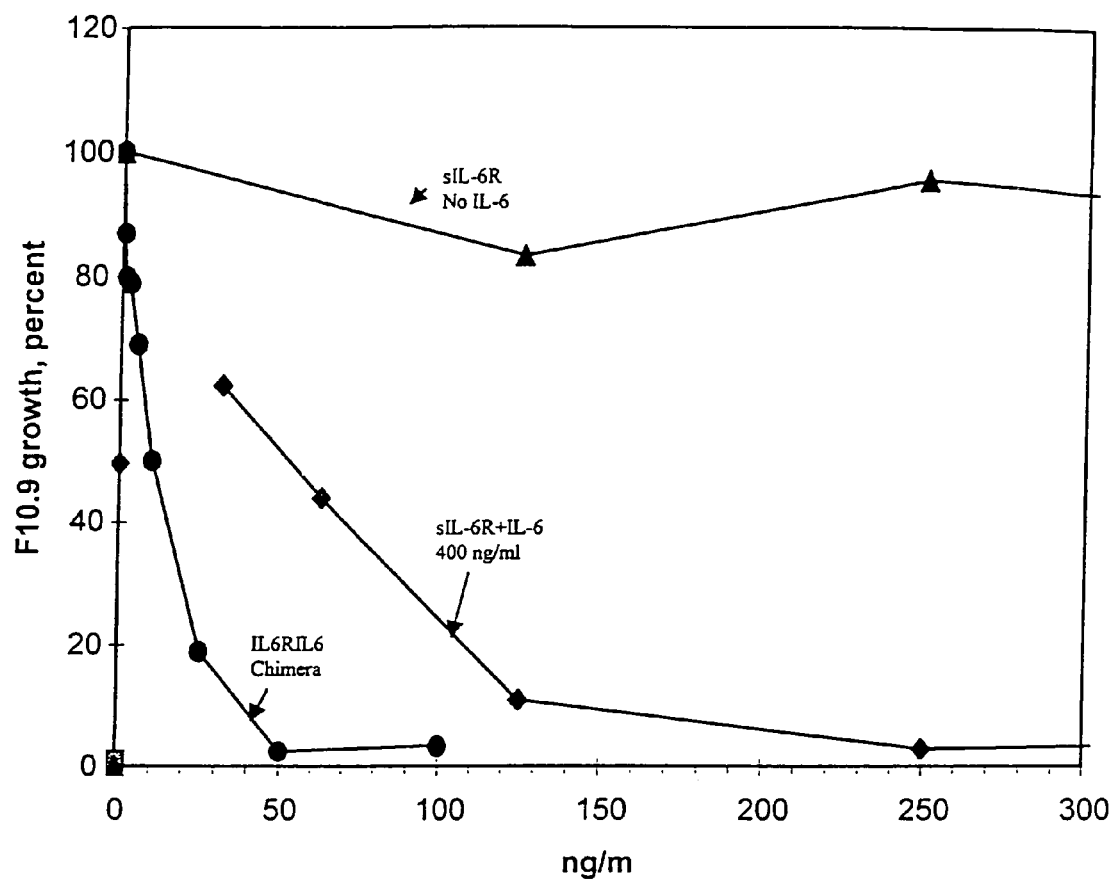
FIG. 9 shows the higher activity of the sIL-6R/IL-6 chimera on F10.9 melanoma cells as compared to the one of the mixture of sIL-6R+IL-6, or to the one of sIL-6R (without IL-6)

CHO-produced IL-6R/IL-6 chimera and a mixture of human IL-6 and sIL-6R were compared for their binding to the soluble form of gp130(sgp 130), which is the second chain of the receptor system for IL-6 (see background). A microtiter 96-well plate (Nunc) was coated with anti-human gp130 monoclonal antibody and 50 ng/ml of sgp130(both from R&D Systems, Minneapolis) was added. After washing in phosphate buffered saline, the IL-6R/IL-6 chimera was added in different wells at different concentrations ranging from 0.1 to 50 ng/ml. In separate wells, rhuIL-6 (Ares-Serono, Geneva) was added at 500 ng/ml together with human sIL-6RδVal at concentrations from 2 to 500 ng/ml. After incubation overnight at 4° C., a rabbit polyclonal anti-IL-6R (Oh et al., Cytokine, 8, 401–409, 1996) was added, followed by goat antirabbit Ig conjugated with horseradish peroxidase which was detected by colored reaction (Sigma, St. Louis). FIG. 8 shows a Scatchard plot of the results. The affinity of the IL-6R/IL-6 chimera to gp130 was found to be over 4 fold higher than that of the two parts of the molecule added separately ($6.3 \times 10^{-11}$M versus $2.6 \times 10^{-10}$M). This result is in line and explains the higher activity of the chimera as compared to the IL-6+sIL-6R combination on melanoma and on hematopoietic cells (FIG. 9 and Example 4).

EXAMPLE 8

The IL-6R/IL-6 Chimera Protects from Hepatotoxicity

Figure 10:
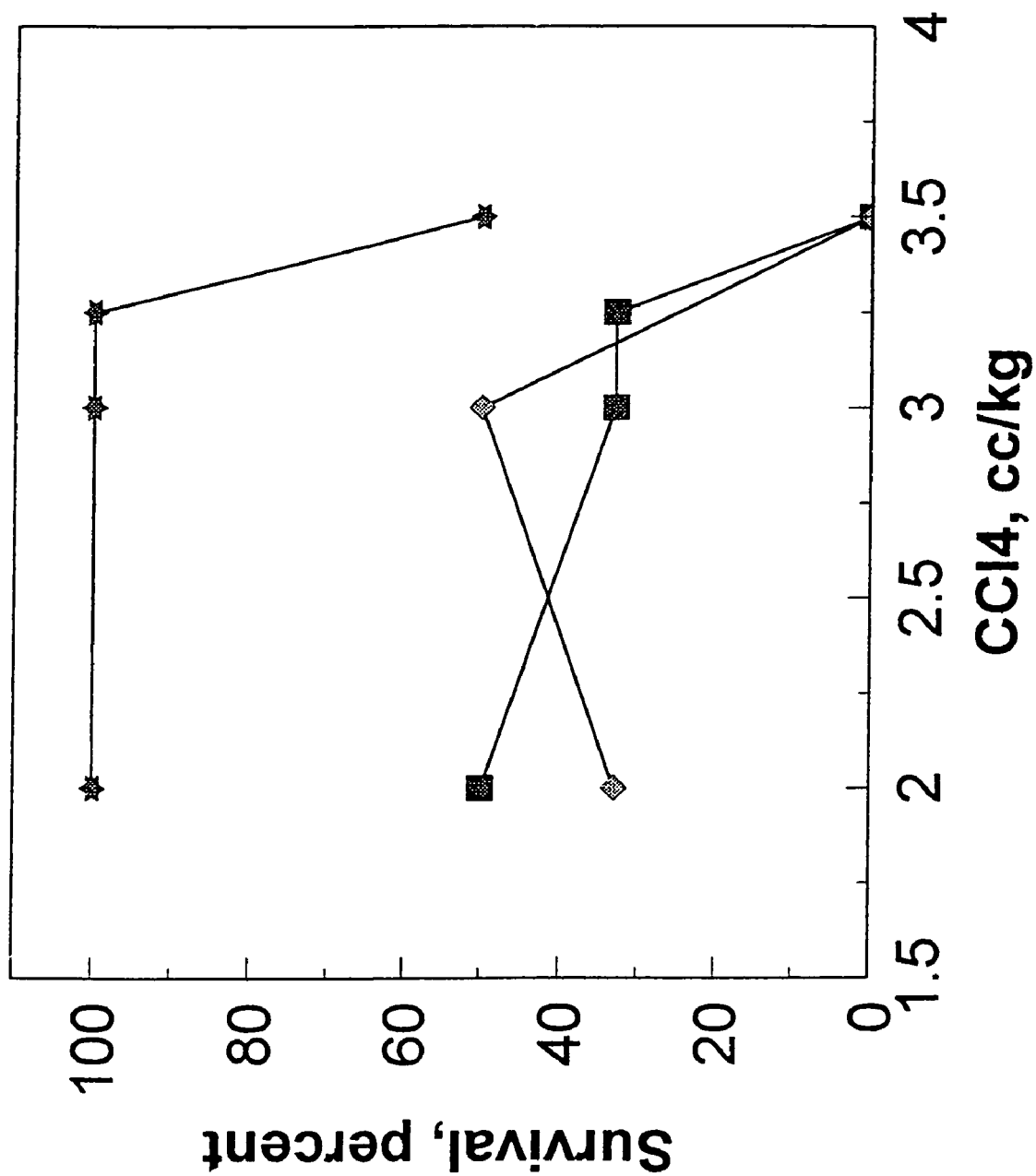
FIG. 10 shows the sIL-6R/IL-6 chimera protection against liver toxicity, the values representing a mean of 4 experiments, filled squares representing IL-6−/− mice, filled diamonds representing IL-6−/− mice receiving IL-6, and filled stars representing IL-6−/− mice receiving the chimera.

Carbon tetrachloride ($CCl_4$) injection to mice produces a severe necrosis of the liver leading to death of the animals (Slater T. F. et al., Philos. Trans. R. Soc. Biol. Sci. 311, 633–645, 1985). When mice which are genetically deficient in IL-6 (IL-6$^{-/-}$) are given relatively low doses of $CCl_4$ (2–3 ml/kg body weight) by intraperitoneal injection, lethality rates at 24 hours are around 70% (FIG. 10). Injection of the CHO-produced IL-6R/IL-6 chimera one hour before $CCl_4$ and again 4 hours after $CCl_4$, protects the animals and no deaths are seen at 24 hours. In contrast, free rhuIL-6 injected similarly has no effect (FIG. 10). The IL-6R/IL-6 chimera was effective at doses of 2–3 μg per injection, which in molar ratio are 10 times lower than the dose of IL-6, which was not effective. At higher doses of $CCl_4$ (e.g. 3.5 ml/kg in FIG. 10), the chimera was also protective, the mortality being lower than with IL-6 or without cytokine. The difference in mortality between mice treated with chimera and untreated mice, both receiving the same $CCl_4$ challenge, was significant at $p<0.01$. Histological observation of liver sections stained with hematoxillin-eosin confirmed that $CCl_4$ produced liver tissue necrosis, and that IL-6R/IL-6 chimera protects the hepatocytes from this chemical toxic effect (not shown).

An application of the IL-6R/IL-6 chimera may be for protection of liver tissue in patients with necrotic diseases due to chemicals (e.g. alcohol, paracetamol) or other causes (e.g. viral hepatitis).

EXAMPLE 9

Construction and Activity of IL-6/sIL-6RδVal Chimera

A chimeric molecule in which the IL-6 moiety is at the N-terminal whereas the sIL-6R moiety is at the C-terminal was constructed. Plasmid pBS-sIL-6RδVal was cut at Sau3a (bp 1086) and at the HindIII following the stop codon after Val-356 (see Example 1). A linker containing three restriction sites: SpeI, SmaI and BamH1 was synthesized as follows:

```
       SpeI         SmaI            BamH1
5' CT AGT GGG CCC GGG GTG GCG GG
(SEQ ID NO:2)

A CCC GGG CCC CAC CGC CCC TAG 5'
(SEQ ID NO:12)
```

This Sau3a site of sIL-6R was ligated to the BamH1 of the linker and cloned in the multiple cloning site of a Bluescript pBS SK plasmid. The IL-6 sequence was amplified by PCR from pKKβ2-7 DNA using the primers (initiation codon underlined):

```
              SpeI
Forward 5' GA CTA GTA GCT ATG AAC TCC TTC TC
(SEQ ID NO:3)

HaeIII
Backward 5' AG GGC CAT TTG CCG AAG AGC C
(SEQ ID NO:4)
```

The PCR product cut with SpeI and HaeIII was introduced between the SpeI and SmaI site of the above linker. Another linker BamH1-NcoI with an internal SmaI was synthesized as follows:

```
                                          SmaI
5' GAT CCG GGC GGC GGG GGA GGG GGG CCC GGG C[NcoI]
(SEQ ID NO:5)

[BamH1] GC CCG CCG CCC CCT CCT CCC GGG CCC GGT AC
5' (SEQ ID NO:11)
```

This was cloned between the BamH1 of the previous linker and the NcoI 1464 of the IL-6R sequence. A fragment of IL-6R from SmaI 867 to NcoI 1464 was then introduced between the SmaI of the second linker and the NcoI of IL-6R. The resulting chimeric DNA was sequenced and recloned in pCDNA3 for expression in human HEK 293 cells. The amino acid sequence of this IL-6-IL-6R chimera 3e is shown in FIG. 11 (linker underlined). Chimera 3e was purified by affinity chromatography on an anti-IL-6 monoclonal antibody (as in Novick et al., Hybridoma 8, 561–567, 1989). On SDS-PAGE, a 75 kDa band was observed.

Figure 12:
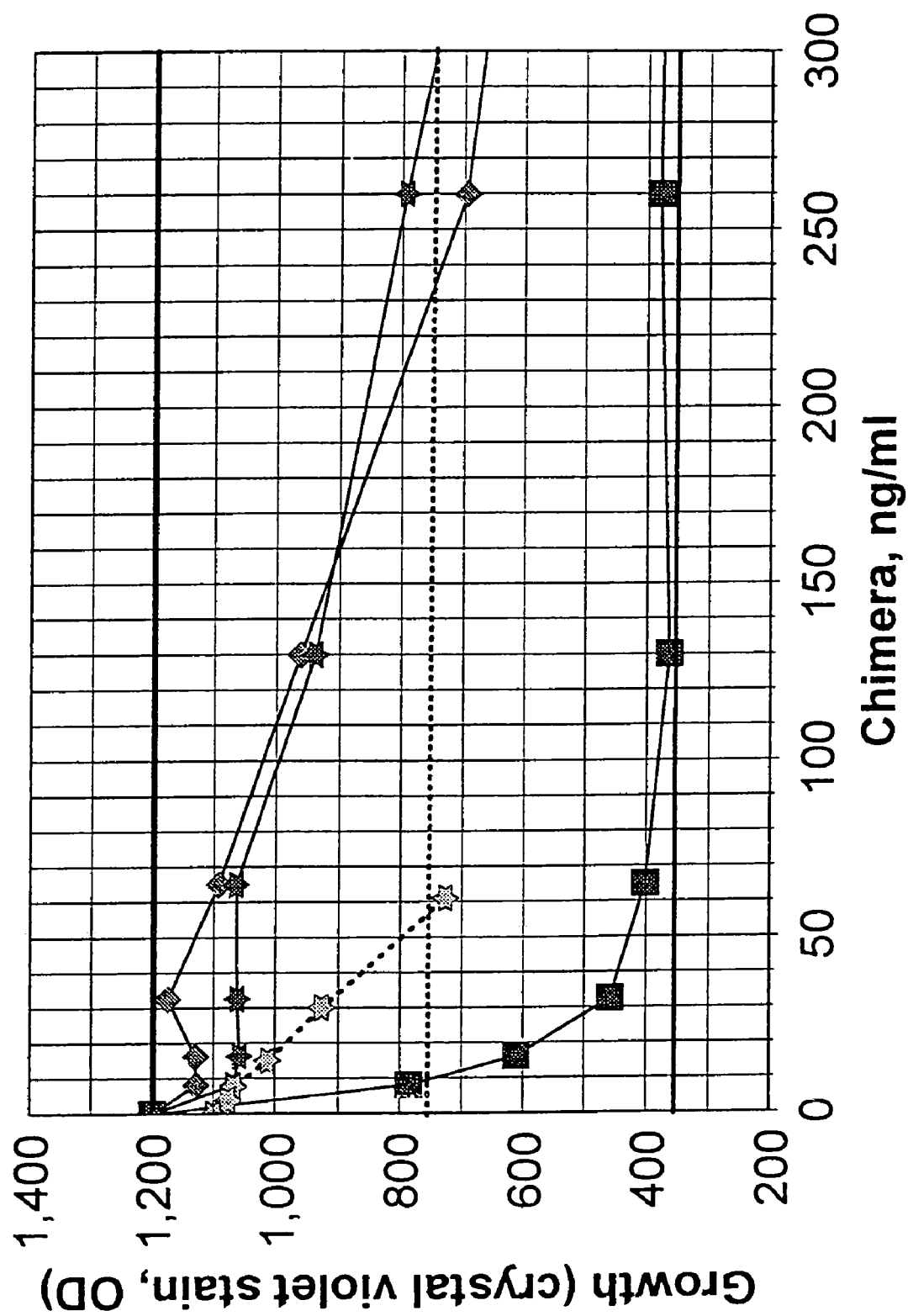
FIG. 12 shows the biological activity on F10.9 melanoma cells of the chimera 3e (dark filled stars) compared to the sIL-6R/IL-6 chimera (filled squares) and two mutants (Mutt 39 (HD)—filled diamonds) and Mutt NHD—light filled stars), as described in Example 9.

The biological activity of the IL-6-IL-6R chimera 3e to inhibit the growth of the F10.9 melanoma cells is shown in FIG. 12. It is clearly active as compared to the IL-6R/IL-6 chimera (preparation 1–3) in the same experiment, although more is required for 50% growth inhibition.

Two mutants of IL-6R/IL-6 were made in which amino acids His-280 and Asp-281 of the IL-6R moiety of IL-6R/IL-6 (FIG. 3) were changed to Ser and Val respectively by PCR mutagenesis (Mutant 39 or HD), or where Asn-230 was in addition changed to Asp (Mutant NHD). As can be seen from FIG. 12, these two mutants had almost no activity as compared to the IL-6R/IL-6 and IL-6-IL-6R chimeras. Since in IL-6R, these amino acid interact with gp130, as shown by molecular modeling (Halimi et al., 1995), this demonstrates that the sIL-6R/IL-6 chimera conserves this essential interaction site.

The IL-6-IL-6R chimera 3e is missing the immunoglobulin-like domain of IL-6R which is present in IL-6R/IL-6. However, just removing this Ig-domain from IL-6R/IL-6 did not reduce its biological activity on F10.9 cells. The binding of IL-6-IL-6R chimera 3e to gp130 was about 30% of that of another IL-6R/IL-6 chimera (not shown). This lower binding is in line with the lower activity on the melanoma cell growth.

These results demonstrate that the blocking of IL-6 carboxyterminus by fusion through a linker to sIL-6R, conserves a good biological activity in such novel chimeras.

REFERENCES

Chen L, Mory Y, Zilberstein A and Revel M. Growth inhibition of human breast carcinoma and leukemia/lymphoma cell lines by recombinant interferon-beta 2/IL-6. Proc. Natl. Acad. Sci. USA, 85: 8037–8041, 1988.

Chernajovsky Y, Mory Y, Chen L, Marks Z, Novick D, Rubinstein M and Revel M. Efficient constitutive production of human fibroblast interferon by hamster cells transformed with the IFN-β1 gene fused to an SV40 early promoter. DNA, 3: 297–308, 1984.

Fischer M, Goldschmitt J, Peschel C, Brakenhoff J P G, Kallen K -J, Wollmer A, Grotzinger J and Rose-John S. A bioactive designer cytokine for human hematopoietic progenitor cell expansion. Nature Biotechnology 15: 142–145, 1997.

Ganaphthi M K, Weizer A K, Borsellino S, Bukowski R M, Ganaphthi S, Rice T, Casey G and Kawamura K. Resistance to Interleukin-6 in human Non-small cell lung carcinoma cell lines: Role of receptor components. Cell Growth and Differentiation, 7: 923–929, 1996.

Halimi H, Eisenstein M, Oh J, Revel M and Chebath J. Epitope peptides from interleukin-6 receptor which inhibit the growth of human myeloma cells. Eur. Cytokine Netw., 6: 135–143, 1995.

Hirano T, Yasukawa K, Harada H, Taga T, Watanabe Y, Matsuda T, Kashimura S, Nakajima K, Koyama K, Iwamatsu K, Tsunasawa S, Sakiyama F, Matsui H, Takahara Y, Taniguchi T and Kishimoto T. Complementary DNA for a novel interleukin (BSF-2) that induces B lymphocytes to produce immunoglobulins. Nature, 234: 73–76, 1986.

Hirano T, Matsuda T and Nakajima K. Signal transduction through gp130 that is shared among the receptors for the interleukin 6 related cytokine subfamily. Stem cells, 12:262–277, 1994.

Holloway C J. Applications of recombinant DNA technology in the production of glycosylated recombinant human granulocyte colony stimulating factor. Eur. J. Cancer, 30: S2–6, 1994.

Kahn M A and De Vellis J. Regulation of an oligodendrocyte progenitor cell line by the interleukin-6 family of cytokines. Glia, 12: 87–98, 1994.

Katz A, Shulman L M, Porgador A, Revel M, Feldman M and Eisenbach L. Abrogation of B16 melanoma metastases by long-term low-dose Interleukin-6 therapy. J. Immunother. 13: 98–109, 1993.

Mackiewicz A, Wiznerowicz M, Roeb E, Nowak J, Pawlowski T, Baumann H, Heinrich P and Rose-John S. Interleukin-6-type cytokines and their receptors for gene therapy of melanoma. Ann. New York Acad. Sci., 762: 361–374, 1995.

McKenna H J, de Vries P, Brasel K, Lyman S D and Williams D E. Effect of flt3 ligand on the ex vivo expansion of human CD34+ hematopoietic progenitor cells. Blood 86: 3413–3420, 1995.

Murakami M, Hibi M, Nakagawa N, Nagakawa T, Yasukawa K, Yamanishi K, Taga T and Kishimoto T. IL-6 induced homodimerization of gp130 and associated activation of a tyrosine kinase. Science, 260: 1808–1810, 1993.

Novick D, Englemann H, Wallach D, Leitner O, Revel M and Rubinstein M. Purification of soluble cytokine receptors from normal urine by ligand-affinity and immunoaffinity chromatography. J. Chromatogr., 510: 331–337, 1990.

Novick D, Engelmann H, Revel M, Leitner O and Rubinstein M. Monoclonal antibodies to the soluble IL-6 receptor: affinity purification, ELISA and inhibition of ligand binding. Hybridoma, 10: 137–146, 1991.

Novick D, Shulman L M, Chen L and Revel M. Enhancement of interleukin-6 cytostatic effect on human breast carcinoma cells by soluble IL-6 receptor from urine and reversion by monoclonal antibodies. Cytokine, 4: 6–11, 1992.

Oh J -W, Revel M and Chebath J. A soluble interleukin-6 receptor isolated from conditioned medium of human breast cancer cells is encoded by a differentially spliced mRNA. Cytokine, 8: 401–409, 1996.

Oh J -W. Expression of recombinant soluble human interleukin-6 receptors and analysis of their functions. Ph.D. Thesis Weizmann Institute of Science (Revel M, supervisor), 1997.

Paonessa G, Graziani R, DeSerio A, Savino R, Ciapponi L, Lahmm A, Salvati A L, Toniatti C and Ciliberto G. Two distinct and independent sites on IL-6 trigger gp130 dimer formation and signalling. EMBO J., 14: 1942–1951, 1995.

Revel M. Host defense against infections and inflammations: Role of the multifunctional IL-6/IFN-β2 cytokine. Experientia 45: 549–557, 1989.

Sambrook J, Fritsch E F and Maniatis T. Molecular cloning: A laboratory manual. Cold Spring Harbor Press, 1989.

Sui X, Tsuji K, Tanaka R, Tajima S, Muraoka K, Ebihara Y, Ikebuchi K, Yasukawa K, Taga T, Kishimoto T and Nakahata T. Gp130 and c-kit signalings synergize for ex vivo expansion of human primitive hemopoietic progenitor cells. Proc. Natl. Acad. Sci. USA 92: 2859–2863, 1995.

Taga T, Hibi M, Hirata Y, Yamasaki K, Yasukawa K, Matsuda T, Hirano T and Kishimoto T. Interleukin-6 triggers the association of its receptor with a possible signal transducer gp130. Cell, 58: 573–581, 1989.

Vormoor J, Lapidot T, Pflumio F, Risdon G, Patterson B, Broxmeyer H E and Dick J E. SCID mice as an in vivo model of human cord blood hematopoiesis. Blood cells 20: 316–320, 1994.

Ward L D, Howlett G J, Discolo G, Yasukawa K, Hammacher A, Moritz R L and Simpson R J. High affinity interleukin-6 receptor is a hexameric complex consisting of two molecules each of interleukin-6, interleukin-6 receptor and gp130. J. Biol. Chem., 269: 23286–23289, 1994.

Yamasaki K, Taga T, Hirata Y, Yawata H, Kawanishi Y, Seed B, Taniguchi T, Hirano T and Kishimoto T. Cloning and expression of the human Interleukin-6 (BSF-2/Interferon beta-2) receptor. Science, 241: 825–828, 1988.

Zilberstein A, Ruggieri R, Korn H J and Revel M. Structure and expression of of cDNA and genes for human interferon-beta-2, a distinct species inducible by growth-stimulatory cytokines. EMBO J., 5: 2529–2537, 1986.

---

The invention claimed is:

1. A chimeric glycosylated soluble interleukin-6 receptor (sIL-6R)—interleukin-6 (IL-6) polypeptide (sIL-6R/IL-6) consisting of:

an amino acid sequence which is a fusion product of sIL-6RδVal fused to IL-6, including a non-immunogenic linker therebetween that is a tripeptide of the sequence Glu-Phe-Met, said chimeric polypeptide having the sequence of SEQ ID NO:7 or an amino acid sequence which is a fusion product of sIL-6RδVal fused to IL-6, that includes a peptide of 13 amino acid residues of sequence Glu-Phe-Gly-Ala- Gly-Leu-Val-Leu-Gly-Gly-Gln-Phe-Met (SEQ ID NO:1) as the linker therebetween, said chimeric polypeptide having the sequence of SEQ ID NO:13, wherein the linker does not prevent the chimeric polypeptide from triggering dimerization of gp130 in human cells.

2. A chimeric sIL-6R/IL-6 according to claim 1, wherein said linker is a tripeptide of the sequence Glu-Phe-Met, said chimeric polypeptide having the sequence of SEQ ID NO:7.

3. A chimeric sIL-6R/IL-6 polypeptide according to claim 1, wherein the linker is a peptide of 13 amino acid residues of sequence Glu-Phe-Gly-Ala-Gly-Leu-Val-Leu-Gly-Gly-Gln-Phe-Met (SEQ ID NO:1), said chimeric polypeptide having the sequence of SEQ ID NO:13.

4. A chimeric sIL-6R/IL-6 according to claim 1, wherein said sIL-6R/IL-6 is produced in mammalian cells.

5. A chimeric sIL-6R/IL-6 protein according to claim 4, wherein said sIL-6R/IL-6 is produced in human cells.

6. A chimeric sIL-6R/IL-6 according to claim 4, wherein said sIL-6R/IL-6 is produced in CHO cells.

7. A pharmaceutical composition comprising as active ingredient a chimeric sIL-6R/IL-6 according to claim 1, and a pharmaceutically acceptable carrier, diluent or excipient.

* * * * *

SEQUENCE LISTING

```
<160> NUMBER OF SEQ ID NOS: 13

<210> SEQ ID NO 1
<211> LENGTH: 13
<212> TYPE: PRT
<213> ORGANISM: Artificial Sequence
<220> FEATURE:
<223> OTHER INFORMATION: synthetic

<400> SEQUENCE: 1

Glu Phe Gly Ala Gly Leu Val Leu Gly Gly Gln Phe Met
1               5                   10

<210> SEQ ID NO 2
<211> LENGTH: 22
<212> TYPE: DNA
<213> ORGANISM: Artificial Sequence
<220> FEATURE:
<223> OTHER INFORMATION: synthetic

<400> SEQUENCE: 2
ctagtgggcc cggggtggcg gg                                              22

<210> SEQ ID NO 3
<211> LENGTH: 25
<212> TYPE: DNA
<213> ORGANISM: Artificial Sequence
<220> FEATURE:
<223> OTHER INFORMATION: synthetic

<400> SEQUENCE: 3
gactagtagc tatgaactcc ttctc                                           25

<210> SEQ ID NO 4
<211> LENGTH: 21
<212> TYPE: DNA
<213> ORGANISM: Artificial Sequence
<220> FEATURE:
<223> OTHER INFORMATION: synthetic

<400> SEQUENCE: 4
agggccattt gccgaagagc c                                               21

<210> SEQ ID NO 5
<211> LENGTH: 31
<212> TYPE: DNA
<213> ORGANISM: Artificial Sequence
<220> FEATURE:
<223> OTHER INFORMATION: synthetic

<400> SEQUENCE: 5
gatccgggcg gcgggggagg ggggcccggg c                                    31

<210> SEQ ID NO 6
<211> LENGTH: 14
```

```
<212> TYPE: PRT
<213> ORGANISM: Artificial Sequence
<220> FEATURE:
<223> OTHER INFORMATION: synthetic

<400> SEQUENCE: 6

Gly Gly Gly Gly Asp Pro Gly Gly Gly Gly Pro Gly
1               5                   10

<210> SEQ ID NO 7
<211> LENGTH: 543
<212> TYPE: PRT
<213> ORGANISM: Artificial Sequence
<220> FEATURE:
<223> OTHER INFORMATION: synthetic

<400> SEQUENCE: 7

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320
```

```
Pro Pro Ala Glu Asn Glu Val Ser Thr Pro Met Gln Ala Leu Thr Thr
            325                 330                 335

Asn Lys Asp Asp Asn Ile Leu Phe Arg Asp Ser Ala Asn Ala Thr
        340                 345                 350

Ser Leu Pro Val Glu Phe Met Pro Val Pro Gly Glu Asp Ser Lys
        355                 360                 365

Asp Val Ala Ala Pro His Arg Gln Pro Leu Thr Ser Glu Arg Ile
        370                 375                 380

Asp Lys Gln Ile Arg Tyr Ile Leu Asp Gly Ile Ser Ala Leu Arg Lys
385                 390                 395                 400

Glu Thr Cys Asn Lys Ser Asn Met Cys Glu Ser Ser Lys Glu Ala Leu
                405                 410                 415

Ala Glu Asn Asn Leu Asn Leu Pro Lys Met Ala Glu Lys Asp Gly Cys
                420                 425                 430

Phe Gln Ser Gly Phe Asn Glu Glu Thr Cys Leu Val Lys Ile Ile Thr
                435                 440                 445

Gly Leu Leu Glu Phe Glu Val Tyr Leu Glu Tyr Leu Gln Asn Arg Phe
450                 455                 460

Glu Ser Ser Glu Glu Gln Ala Arg Ala Val Gln Met Ser Thr Lys Val
465                 470                 475                 480

Leu Ile Gln Phe Leu Gln Lys Lys Ala Lys Asn Leu Asp Ala Ile Thr
                485                 490                 495

Thr Pro Asp Pro Thr Thr Asn Ala Ser Leu Leu Thr Lys Leu Gln Ala
                500                 505                 510

Gln Asn Gln Trp Leu Gln Asp Met Thr Thr His Leu Ile Leu Arg Ser
                515                 520                 525

Phe Lys Glu Phe Leu Gln Ser Ser Leu Arg Ala Leu Arg Gln Met
                535                 540
```

<210> SEQ ID NO 8
<211> LENGTH: 471
<212> TYPE: PRT
<213> ORGANISM: Artificial Sequence
<220> FEATURE:
<223> OTHER INFORMATION: synthetic

<400> SEQUENCE: 8

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140
```

```
Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
            165                 170                 175

Thr Lys Leu Gln Ala Gln Asn Gln Trp Leu Gln Asp Met Thr Thr His
        180                 185                 190

Leu Ile Leu Arg Ser Phe Lys Glu Phe Leu Gln Ser Ser Leu Arg Ala
    195                 200                 205

Leu Arg Gln Met Gly Gly Gly Gly Asp Pro Gly Gly Gly Gly Gly Gly
210                 215                 220

Pro Gly Val Pro Pro Glu Glu Pro Gln Leu Ser Cys Phe Arg Lys Ser
225                 230                 235                 240

Pro Leu Ser Asn Val Val Cys Glu Trp Gly Pro Arg Ser Thr Pro Ser
            245                 250                 255

Leu Thr Thr Lys Ala Val Leu Leu Val Arg Lys Phe Gln Asn Ser Pro
        260                 265                 270

Ala Glu Asp Phe Gln Glu Pro Cys Gln Tyr Ser Gln Glu Ser Gln Lys
    275                 280                 285

Phe Ser Cys Gln Leu Ala Val Pro Glu Gly Asp Ser Ser Phe Tyr Ile
290                 295                 300

Val Ser Met Cys Val Ala Ser Ser Val Gly Ser Lys Phe Ser Lys Thr
305                 310                 315                 320

Gln Thr Phe Gln Gly Cys Gly Ile Leu Gln Pro Asp Pro Pro Ala Asn
            325                 330                 335

Ile Thr Val Thr Ala Val Ala Arg Asn Pro Arg Trp Leu Ser Val Thr
        340                 345                 350

Trp Gln Asp Pro His Ser Trp Asn Ser Ser Phe Tyr Arg Leu Arg Phe
    355                 360                 365

Glu Leu Arg Tyr Arg Ala Glu Arg Ser Lys Thr Phe Thr Thr Trp Met
370                 375                 380

Val Lys Asp Leu Gln His His Cys Val Ile His Asp Ala Trp Ser Gly
385                 390                 395                 400

Leu Arg His Val Val Gln Leu Arg Ala Gln Glu Glu Phe Gly Gln Gly
            405                 410                 415

Glu Trp Ser Glu Trp Ser Pro Glu Ala Met Gly Thr Pro Trp Thr Glu
        420                 425                 430

Ser Arg Ser Pro Pro Ala Glu Asn Glu Val Ser Thr Pro Met Gln Ala
    435                 440                 445

Leu Thr Thr Asn Lys Asp Asp Asp Asn Ile Leu Phe Arg Asp Ser Ala
450                 455                 460

Asn Ala Thr Ser Leu Pro Val
465                 470

<210> SEQ ID NO 9
<211> LENGTH: 24
<212> TYPE: DNA
<213> ORGANISM: Artificial Sequence
<220> FEATURE:
<223> OTHER INFORMATION: synthetic

<400> SEQUENCE: 9
gcgacaagcc tcccagtgga attc                                      24

<210> SEQ ID NO 10
<211> LENGTH: 18
```

-continued

```
<212> TYPE: DNA
<213> ORGANISM: Artificial Sequence
<220> FEATURE:
<223> OTHER INFORMATION: synthetic

<400> SEQUENCE: 10
cagtacccga attcatgc                                                   18

<210> SEQ ID NO 11
<211> LENGTH: 31
<212> TYPE: DNA
<213> ORGANISM: Artificial Sequence
<220> FEATURE:
<223> OTHER INFORMATION: synthetic

<400> SEQUENCE: 11
catggcccgg gccctcctcc cccgccgccc g                                    31

<210> SEQ ID NO 12
<211> LENGTH: 22
<212> TYPE: DNA
<213> ORGANISM: Artificial Sequence
<220> FEATURE:
<223> OTHER INFORMATION: synthetic

<400> SEQUENCE: 12
gatccccgcc accccgggcc ca                                              22

<210> SEQ ID NO 13
<211> LENGTH: 553
<212> TYPE: PRT
<213> ORGANISM: Artificial
<220> FEATURE:
<223> OTHER INFORMATION: synthetic

<400> SEQUENCE: 13
```

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

|     |     |     |     |     |     |     |     |     |     |     |     |
| --- | --- | --- | --- | --- | --- | --- | --- | --- | --- | --- | --- |
| Cys | Val | Ala | Ser | Ser | Val | Gly | Ser | Lys | Phe | Ser | Lys | Thr | Gln | Thr | Phe |
|     | 195 |     |     |     | 200 |     |     |     |     | 205 |     |

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225             230                 235                 240

Pro His Ser Trp Asn Ser Ser Phe Tyr Arg Leu Arg Phe Glu Leu Arg
            245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
            290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Glu Phe Gly Ala Gly Leu Val Leu Gly Gly Gln Phe
            355                 360                 365

Met Pro Val Pro Pro Gly Glu Asp Ser Lys Asp Val Ala Ala Pro His
    370                 375                 380

Arg Gln Pro Leu Thr Ser Glu Arg Ile Asp Lys Gln Ile Arg Tyr
385             390                 395                 400

Ile Leu Asp Gly Ile Ser Ala Leu Arg Lys Glu Thr Cys Asn Lys Ser
                405                 410                 415

Asn Met Cys Glu Ser Ser Lys Glu Ala Leu Ala Glu Asn Asn Leu Asn
            420                 425                 430

Leu Pro Lys Met Ala Glu Lys Asp Gly Cys Phe Gln Ser Gly Phe Asn
    435                 440                 445

Glu Glu Thr Cys Leu Val Lys Ile Ile Thr Gly Leu Leu Glu Phe Glu
    450                 455                 460

Val Tyr Leu Glu Tyr Leu Gln Asn Arg Phe Glu Ser Ser Glu Glu Gln
465             470                 475                 480

Ala Arg Ala Val Gln Met Ser Thr Lys Val Leu Ile Gln Phe Leu Gln
                485                 490                 495

Lys Lys Ala Lys Asn Leu Asp Ala Ile Thr Thr Pro Asp Pro Thr Thr
            500                 505                 510

Asn Ala Ser Leu Leu Thr Lys Leu Gln Ala Gln Asn Gln Trp Leu Gln
            515                 520                 525

Asp Met Thr Thr His Leu Ile Leu Arg Ser Phe Lys Glu Phe Leu Gln
    530                 535                 540

Ser Ser Leu Arg Ala Leu Arg Gln Met
545             550